US012633380B2

(12) United States Patent
Pauly et al.

(10) Patent No.: US 12,633,380 B2
(45) Date of Patent: May 19, 2026

(54) SYSTEMS AND METHODS FOR CLASSIFICATION OF RADIATION ENERGY SPECTRA

(71) Applicant: Rapiscan Holdings, Inc., Hawthorne, CA (US)

(72) Inventors: Steven Wayne Pauly, Knoxville, TN (US); William Mark Richardson, Knoxville, TN (US); Phillip John Boone, Lenoir City, TN (US)

(73) Assignee: Rapiscan Holdings, Inc., Torrance, CA (US)

( * ) Notice: Subject to any disclaimer, the term of this patent is extended or adjusted under 35 U.S.C. 154(b) by 295 days.

(21) Appl. No.: 18/363,345

(22) Filed: Aug. 1, 2023

(65) Prior Publication Data

US 2024/0312572 A1 Sep. 19, 2024

Related U.S. Application Data

(60) Provisional application No. 63/374,272, filed on Sep. 1, 2022.

(51) Int. Cl.
*G16C 20/10* (2019.01)
(52) U.S. Cl.
CPC .................................. *G16C 20/10* (2019.02)
(58) Field of Classification Search
CPC .. G01T 1/167; G01T 1/36; G01T 1/16; G01T 1/17; G01T 1/40; G01T 1/161;
(Continued)

(56) References Cited

U.S. PATENT DOCUMENTS 2,636,619 A 4/1953 Alexander
2,831,123 A 4/1958 Daly
(Continued)

FOREIGN PATENT DOCUMENTS

AT 406586 T 9/2008
AT 553401 T 4/2012
(Continued)

OTHER PUBLICATIONS

"Mobile X-Ray Inspection Systems" Internet citation Feb. 12, 2007, pp. 1-2, XP007911046 Retrieved from the Internet: URL:http://web. archive.org/web/20070212000928/http://www.bombdetection.co-m/cat. sub.--details.php?catid=20> [retrieved on Jan. 6, 2010].
(Continued)

*Primary Examiner* — David J Makiya
*Assistant Examiner* — Soorena Kefayati
(74) *Attorney, Agent, or Firm* — Novel IP

(57) ABSTRACT

A method of determining if a radiation spectra comprises radiation corresponding to naturally occurring radiation material sources (NORM), the method including: gathering the radiation spectra; normalizing the gathered spectra by using one or more predefined normalization techniques; energy scaling the normalized spectra by using one or more energy scaling techniques; and determining materials corresponding to each energy reading in the scaled energy spectra for categorizing the determined materials into one or more predefined categories by using one or more classification algorithms.

19 Claims, 11 Drawing Sheets

(58) Field of Classification Search

CPC ......... G01T 1/163; G01T 7/005; G06F 30/27; G06T 2207/20084; G06T 2207/20081; G08B 13/24; G16C 20/10

See application file for complete search history.

(56) References Cited

U.S. PATENT DOCUMENTS

| | | | |
|---|---|---|---|
| 2,971,433 A | 2/1961 | Akin |
| 3,275,831 A | 9/1966 | Martin |
| 3,374,355 A | 3/1968 | Parratt |
| 3,439,166 A | 4/1969 | Chope |
| 3,676,783 A | 7/1972 | Kinbara |
| 3,766,387 A | 10/1973 | Heffan |
| 3,767,850 A | 10/1973 | Mc Millian |
| 3,770,955 A | 11/1973 | Tomita |
| 3,784,837 A | 1/1974 | Holmstrom |
| 3,837,502 A | 9/1974 | Hornagold |
| 3,904,923 A | 9/1975 | Schwartz |
| 3,988,586 A | 10/1976 | Stuart |
| 4,047,035 A | 9/1977 | Dennhoven |
| 4,139,771 A | 2/1979 | Dennhoven |
| 4,164,138 A | 8/1979 | Burkhart |
| 4,210,811 A | 7/1980 | Dennhoven |
| 4,216,499 A | 8/1980 | Manfred |
| 4,239,969 A | 12/1980 | Galetta |
| 4,366,382 A | 12/1982 | Kotowski |
| 4,430,568 A | 2/1984 | Yoshida |
| 4,563,707 A | 1/1986 | Kishida |
| 4,566,113 A | 1/1986 | Gerhard |
| 4,599,740 A | 7/1986 | Cable |
| 4,626,688 A | 12/1986 | Barnes |
| 4,641,330 A | 2/1987 | Herwig |
| 4,658,408 A | 4/1987 | Amor |
| 4,709,382 A | 11/1987 | Sones |
| 4,736,401 A | 4/1988 | Donges |
| 4,788,704 A | 11/1988 | Donges |
| 4,817,123 A | 3/1989 | Sones |
| 4,825,454 A | 4/1989 | Annis |
| 4,853,595 A | 8/1989 | Alfano |
| 4,872,188 A | 10/1989 | Lauro |
| 4,884,289 A | 11/1989 | Glockmann |
| 4,979,202 A | 12/1990 | Siczek |
| 4,991,189 A | 2/1991 | Boomgaarden |
| 5,006,299 A | 4/1991 | Gozani |
| 5,014,293 A | 5/1991 | Boyd |
| 5,022,062 A | 6/1991 | Annis |
| 5,041,728 A | 8/1991 | Spacher |
| 5,065,418 A | 11/1991 | Bermbach |
| 5,076,993 A | 12/1991 | Sawa |
| 5,091,924 A | 2/1992 | Bermbach |
| 5,098,640 A | 3/1992 | Gozani |
| 5,114,662 A | 5/1992 | Gozani |
| 5,179,581 A | 1/1993 | Annis |
| 5,181,234 A | 1/1993 | Smith |
| 5,182,764 A | 1/1993 | Peschmann |
| 5,185,778 A | 2/1993 | Magram |
| 5,197,088 A | 3/1993 | Vincent |
| 5,202,932 A | 4/1993 | Cambier |
| 5,221,843 A | 6/1993 | Alvarez |
| 5,224,144 A | 6/1993 | Annis |
| 5,237,598 A | 8/1993 | Albert |
| 5,247,561 A | 9/1993 | Kotowski |
| 5,253,283 A | 10/1993 | Annis |
| 5,259,012 A | 11/1993 | Baker |
| 5,313,511 A | 5/1994 | Annis |
| 5,363,940 A | 11/1994 | Fahrion |
| 5,367,552 A | 11/1994 | Peschmann |
| 5,379,334 A | 1/1995 | Zimmer |
| 5,493,596 A | 2/1996 | Annis |
| 5,503,424 A | 4/1996 | Agopian |
| 5,548,123 A | 8/1996 | Perez-Mendez |
| 5,600,303 A | 2/1997 | Husseiny |
| 5,606,167 A | 2/1997 | Miller |
| 5,608,214 A | 3/1997 | Baron |
| 5,638,420 A | 6/1997 | Armistead |
| 5,642,393 A | 6/1997 | Krug |
| 5,642,394 A | 6/1997 | Rothschild |
| 5,666,393 A | 9/1997 | Annis |
| 5,687,210 A | 11/1997 | Maitrejean |
| 5,692,028 A | 11/1997 | Geus |
| 5,692,029 A | 11/1997 | Husseiny |
| 5,751,837 A | 5/1998 | Watanabe |
| 5,764,683 A | 6/1998 | Swift |
| 5,768,334 A | 6/1998 | Maitrejean |
| 5,787,145 A | 7/1998 | Geus |
| 5,805,660 A | 9/1998 | Perion |
| 5,838,759 A | 11/1998 | Armistead |
| 5,842,578 A | 12/1998 | Cordeiro |
| 5,903,623 A | 5/1999 | Swift |
| 5,909,478 A | 6/1999 | Polichar |
| 5,910,973 A | 6/1999 | Grodzins |
| 5,930,326 A | 7/1999 | Rothschild |
| 5,940,468 A | 8/1999 | Huang |
| 5,974,111 A | 10/1999 | Krug |
| 6,031,890 A | 2/2000 | Bermbach |
| 6,056,671 A | 5/2000 | Marmer |
| 6,058,158 A | 5/2000 | Eiler |
| 6,067,344 A | 5/2000 | Grodzins |
| 6,081,580 A | 6/2000 | Grodzins |
| 6,094,472 A | 7/2000 | Smith |
| 6,151,381 A | 11/2000 | Grodzins |
| 6,188,747 B1 | 2/2001 | Geus |
| 6,192,101 B1 | 2/2001 | Grodzins |
| 6,192,104 B1 | 2/2001 | Adams |
| 6,195,413 B1 | 2/2001 | Geus |
| 6,198,795 B1 | 3/2001 | Naumann |
| 6,216,540 B1 | 4/2001 | Nelson |
| 6,218,943 B1 | 4/2001 | Ellenbogexn |
| 6,220,099 B1 | 4/2001 | Marti |
| 6,249,567 B1 | 6/2001 | Rothschild |
| 6,252,929 B1 | 6/2001 | Swift |
| 6,256,369 B1 | 7/2001 | Lai |
| 6,278,115 B1 | 8/2001 | Annis |
| 6,282,260 B1 | 8/2001 | Grodzins |
| 6,292,533 B1 | 9/2001 | Swift |
| 6,301,326 B2 | 10/2001 | Bjorkholm |
| 6,301,327 B1 | 10/2001 | Martens |
| 6,320,933 B1 | 11/2001 | Grodzins |
| 6,347,132 B1 | 2/2002 | Annis |
| 6,356,620 B1 | 3/2002 | Rothschild |
| 6,418,194 B1 | 7/2002 | McPherson |
| 6,424,695 B1 | 7/2002 | Grodzins |
| 6,434,219 B1 | 8/2002 | Rothschild |
| 6,435,715 B1 | 8/2002 | Betz |
| 6,442,233 B1 | 8/2002 | Grodzins |
| 6,445,765 B1 | 9/2002 | Frank |
| 6,448,564 B1 | 9/2002 | Johnson |
| 6,453,003 B1 | 9/2002 | Springer |
| 6,453,007 B2 | 9/2002 | Adams |
| 6,456,684 B1 | 9/2002 | Mun |
| 6,459,761 B1 | 10/2002 | Grodzins |
| 6,459,764 B1 | 10/2002 | Chalmers |
| 6,473,487 B1 | 10/2002 | Le |
| RE37,899 E | 11/2002 | Grodzins |
| 6,483,894 B2 | 11/2002 | Hartick |
| 6,507,025 B1 | 1/2003 | Verbinski |
| 6,532,276 B1 | 3/2003 | Hartick |
| 6,542,574 B2 | 4/2003 | Grodzins |
| 6,542,578 B2 | 4/2003 | Ries |
| 6,542,580 B1 | 4/2003 | Carver |
| 6,546,072 B1 | 4/2003 | Chalmers |
| 6,552,346 B2 | 4/2003 | Verbinski |
| 6,563,903 B2 | 5/2003 | Kang |
| 6,580,778 B2 | 6/2003 | Meder |
| 6,584,170 B2 | 6/2003 | Aust |
| 6,597,760 B2 | 7/2003 | Beneke |
| 6,606,516 B2 | 8/2003 | Levine |
| 6,614,872 B2 | 9/2003 | Bueno |
| 6,636,581 B2 | 10/2003 | Sorenson |
| 6,653,588 B1 | 11/2003 | Gillard-Hickman |
| 6,658,087 B2 | 12/2003 | Chalmers |
| 6,663,280 B2 | 12/2003 | Doenges |
| 6,665,373 B1 | 12/2003 | Kotowski |
| 6,665,433 B2 | 12/2003 | Roder |

(56) References Cited

U.S. PATENT DOCUMENTS

| | | | |
|---|---|---|---|
| 6,702,459 B2 | 3/2004 | Barnes | |
| 6,713,773 B1 | 3/2004 | Lyons | |
| 6,727,506 B2 | 4/2004 | Mallette | |
| 6,763,635 B1 | 7/2004 | Lowman | |
| 6,785,357 B2 | 8/2004 | Bernardi | |
| 6,812,426 B1 | 11/2004 | Kotowski | |
| 6,816,571 B2 | 11/2004 | Bijjani | |
| 6,837,422 B1 | 1/2005 | Meder | |
| 6,839,134 B2 | 1/2005 | Saito | |
| 6,839,403 B1 | 1/2005 | Kotowski | |
| 6,843,599 B2 | 1/2005 | Le | |
| 6,920,197 B2 | 7/2005 | Kang | |
| 6,924,487 B2 | 8/2005 | Bolozdynya | |
| 6,928,141 B2 | 8/2005 | Carver | |
| 6,940,071 B2 | 9/2005 | Ramsden | |
| 6,944,263 B2 | 9/2005 | Xiao | |
| 6,965,314 B2 | 11/2005 | Bohinc, Jr. | |
| 7,010,094 B2 | 3/2006 | Grodzins | |
| 7,039,159 B2 | 5/2006 | Muenchau | |
| 7,045,788 B2 | 5/2006 | Iwatschenko-Borho | |
| 7,046,768 B1 | 5/2006 | Gilevich | |
| 7,095,326 B2 | 8/2006 | Young | |
| 7,099,434 B2 | 8/2006 | Adams | |
| 7,103,137 B2 | 9/2006 | Seppi | |
| 7,116,235 B2 | 10/2006 | Alioto | |
| RE39,396 E | 11/2006 | Swift | |
| 7,151,447 B1 | 12/2006 | Willms | |
| 7,166,844 B1 | 1/2007 | Gormley | |
| 7,202,478 B2 | 4/2007 | Ramsden | |
| 7,203,276 B2 | 4/2007 | Arsenault | |
| 7,207,713 B2 | 4/2007 | Lowman | |
| 7,215,737 B2 | 5/2007 | Li | |
| 7,215,738 B2 | 5/2007 | Muenchau | |
| 7,218,704 B1 | 5/2007 | Adams | |
| 7,238,951 B2 | 7/2007 | Disdier | |
| 7,239,245 B2 | 7/2007 | Kang | |
| 7,244,947 B2 | 7/2007 | Polichar | |
| 7,260,255 B2 | 8/2007 | Polichar | |
| 7,302,035 B2 | 11/2007 | Hu | |
| 7,322,745 B2 | 1/2008 | Agrawal | |
| 7,352,843 B2 | 4/2008 | Hu | |
| 7,352,844 B1 | 4/2008 | Muenchau | |
| 7,366,282 B2 | 4/2008 | Peschmann | |
| 7,369,643 B2 | 5/2008 | Kotowski | |
| 7,372,040 B2 | 5/2008 | Polichar | |
| 7,379,530 B2 | 5/2008 | Hoff | |
| 7,386,093 B2 | 6/2008 | Wu | |
| 7,388,209 B1 | 6/2008 | Gormley | |
| 7,397,891 B2 | 7/2008 | Johnson | |
| 7,399,976 B2 | 7/2008 | Kang | |
| 7,400,701 B1 | 7/2008 | Cason | |
| 7,400,706 B2 | 7/2008 | Li | |
| 7,417,440 B2 | 8/2008 | Peschmann | |
| 7,418,077 B2 | 8/2008 | Gray | |
| 7,420,174 B2 | 9/2008 | Kurita | |
| 7,453,987 B1 | 11/2008 | Richardson | |
| 7,456,780 B1 | 11/2008 | Garren | |
| 7,470,914 B2 | 12/2008 | Li | |
| 7,471,764 B2 | 12/2008 | Kaval | |
| 7,483,510 B2 | 1/2009 | Carver | |
| 7,483,511 B2 | 1/2009 | Bendahan | |
| 7,486,768 B2 | 2/2009 | Allman | |
| 7,499,522 B2 | 3/2009 | Chen | |
| 7,504,635 B2 | 3/2009 | Ramsden | |
| 7,505,556 B2 | 3/2009 | Chalmers | |
| 7,505,557 B2 | 3/2009 | Modica | |
| 7,508,908 B2 | 3/2009 | Hu | |
| 7,512,212 B2 | 3/2009 | Li | |
| 7,517,149 B2 | 4/2009 | Agrawal | |
| 7,519,148 B2 | 4/2009 | Kotowski | |
| 7,525,101 B2 | 4/2009 | Grodzins | |
| 7,526,064 B2 | 4/2009 | Akery | |
| 7,538,325 B2 | 5/2009 | Mishin | |
| 7,547,887 B2 | 6/2009 | Ramsden | |
| 7,547,888 B2 | 6/2009 | Cooke | |
| 7,555,099 B2 | 6/2009 | Rothschild | |
| 7,570,737 B2 | 8/2009 | Kang | |
| 7,579,845 B2 | 8/2009 | Peschmann | |
| 7,580,505 B2 | 8/2009 | Kang | |
| 7,593,506 B2 | 9/2009 | Cason | |
| 7,593,510 B2 | 9/2009 | Rothschild | |
| 7,596,275 B1 | 9/2009 | Richardson | |
| 7,634,055 B2 | 12/2009 | Hu | |
| 7,647,189 B2 | 1/2010 | Kang | |
| 7,649,976 B2 | 1/2010 | Georgeson | |
| 7,660,388 B2 | 2/2010 | Gray | |
| 7,663,109 B2 | 2/2010 | Kang | |
| 7,683,336 B2 | 3/2010 | Ramsden | |
| 7,684,538 B2 | 3/2010 | Morton | |
| 7,684,541 B2 | 3/2010 | Wang | |
| 7,702,070 B2 | 4/2010 | Kang | |
| 7,720,195 B2 | 5/2010 | Allman | |
| 7,722,251 B2 | 5/2010 | Kang | |
| 7,724,868 B2 | 5/2010 | Morton | |
| 7,724,869 B2 | 5/2010 | Wang | |
| 7,738,687 B2 | 6/2010 | Tortora | |
| 7,741,612 B2 | 6/2010 | Clothier | |
| 7,742,568 B2 | 6/2010 | Smith | |
| 7,760,103 B2 | 7/2010 | Frank | |
| 7,760,852 B2 | 7/2010 | Chen | |
| 7,769,133 B2 | 8/2010 | Carver | |
| 7,783,003 B2 | 8/2010 | Clayton | |
| 7,783,004 B2 | 8/2010 | Kotowski | |
| 7,783,005 B2 | 8/2010 | Kaval | |
| 7,800,073 B2 | 9/2010 | Clothier | |
| 7,807,964 B2 | 10/2010 | Li | |
| 7,809,104 B2 | 10/2010 | Foland | |
| 7,817,775 B2 | 10/2010 | Kang | |
| 7,817,776 B2 | 10/2010 | Agrawal | |
| 7,820,973 B2 * | 10/2010 | Ruan | G01T 7/00 |
| | | | 250/361 R |
| 7,852,981 B2 | 12/2010 | Luo | |
| 7,856,081 B2 | 12/2010 | Peschmann | |
| 7,860,213 B2 | 12/2010 | Akery | |
| 7,864,920 B2 | 1/2011 | Rothschild | |
| 7,876,879 B2 | 1/2011 | Morton | |
| 7,876,880 B2 | 1/2011 | Kotowski | |
| 7,903,789 B2 | 3/2011 | Morton | |
| 7,915,596 B2 | 3/2011 | Clothier | |
| 7,924,975 B2 | 4/2011 | Zhang | |
| 7,928,400 B1 | 4/2011 | Diawara | |
| 7,929,663 B2 | 4/2011 | Morton | |
| 7,942,576 B2 | 5/2011 | Zhao | |
| 7,947,957 B2 | 5/2011 | Ruan | |
| 7,949,101 B2 | 5/2011 | Morton | |
| 7,952,079 B2 | 5/2011 | Neustadter | |
| 7,963,695 B2 | 6/2011 | Kotowski | |
| 7,982,191 B2 | 7/2011 | Friedman | |
| 7,991,113 B2 | 8/2011 | Carver | |
| 7,991,133 B2 | 8/2011 | Mills | |
| 7,995,705 B2 | 8/2011 | Allman | |
| 7,995,707 B2 | 8/2011 | Rothschild | |
| 8,013,297 B2 | 9/2011 | Peng | |
| 8,031,903 B2 | 10/2011 | Paresi | |
| 8,054,938 B2 | 11/2011 | Kaval | |
| 8,059,781 B2 | 11/2011 | Agrawal | |
| 8,073,099 B2 | 12/2011 | Niu | |
| 8,084,748 B2 | 12/2011 | Peng | |
| 8,085,897 B2 | 12/2011 | Morton | |
| 8,094,784 B2 | 1/2012 | Morton | |
| 8,129,691 B2 | 3/2012 | Hu | |
| 8,135,110 B2 | 3/2012 | Morton | |
| 8,138,770 B2 | 3/2012 | Peschmann | |
| 8,170,177 B2 | 5/2012 | Akery | |
| 8,173,970 B2 | 5/2012 | Inbar | |
| 8,204,173 B2 | 6/2012 | Betcke | |
| 8,217,365 B2 | 7/2012 | Chen | |
| 8,223,919 B2 | 7/2012 | Morton | |
| 8,243,876 B2 | 8/2012 | Morton | |
| 8,247,776 B2 | 8/2012 | Peng | |
| 8,263,938 B2 | 9/2012 | Bjorkholm | |
| 8,275,091 B2 | 9/2012 | Morton | |
| 8,288,718 B2 | 10/2012 | Li | |
| 8,319,188 B2 | 11/2012 | Ramsden | |

(56) References Cited

U.S. PATENT DOCUMENTS

| | | | |
|---|---|---|---|
| 8,325,871 | B2 | 12/2012 | Grodzins |
| 8,331,535 | B2 | 12/2012 | Morton |
| 8,345,819 | B2 | 1/2013 | Mastronardi |
| 8,356,937 | B2 | 1/2013 | Kotowski |
| 8,374,310 | B2 | 2/2013 | Kang |
| 8,374,993 | B2 | 2/2013 | Ramsden |
| 8,384,016 | B2 | 2/2013 | Ramsden |
| 8,385,501 | B2 | 2/2013 | Allman |
| 8,389,941 | B2 | 3/2013 | Bendahan |
| 8,389,942 | B2 | 3/2013 | Morton |
| 8,396,189 | B2 | 3/2013 | Kang |
| 8,428,217 | B2 | 4/2013 | Peschmann |
| 8,433,036 | B2 | 4/2013 | Morton |
| 8,439,565 | B2 | 5/2013 | Mastronardi |
| 8,442,186 | B2 | 5/2013 | Rothschild |
| 8,451,974 | B2 | 5/2013 | Morton |
| 8,457,274 | B2 | 6/2013 | Arodzero |
| 8,457,275 | B2 | 6/2013 | Akery |
| 8,477,902 | B2 | 7/2013 | Li |
| 8,483,356 | B2 | 7/2013 | Bendahan |
| 8,491,189 | B2 | 7/2013 | Kotowski |
| 8,503,605 | B2 | 8/2013 | Morton |
| 8,503,606 | B2 | 8/2013 | Rothschild |
| 8,532,823 | B2 | 9/2013 | Mcelroy |
| 8,552,722 | B2 | 10/2013 | Lionheart |
| 8,559,592 | B2 | 10/2013 | Betcke |
| 8,579,506 | B2 | 11/2013 | Morton |
| 8,582,857 | B2 | 11/2013 | Chen |
| 8,625,735 | B2 | 1/2014 | Morton |
| 8,644,453 | B2 | 2/2014 | Morton |
| 8,668,386 | B2 | 3/2014 | Morton |
| 8,674,706 | B2 | 3/2014 | Peschmann |
| 8,679,409 | B2 | 3/2014 | Zhang |
| 8,687,765 | B2 | 4/2014 | Kotowski |
| 8,690,427 | B2 | 4/2014 | Mastronardi |
| 8,735,833 | B2 | 5/2014 | Morton |
| 8,750,452 | B2 | 6/2014 | Kaval |
| 8,774,357 | B2 | 7/2014 | Morton |
| 8,798,232 | B2 | 8/2014 | Bendahan |
| 8,804,899 | B2 | 8/2014 | Morton |
| 8,824,632 | B2 | 9/2014 | Mastronardi |
| 8,824,637 | B2 | 9/2014 | Morton |
| 8,831,176 | B2 | 9/2014 | Morton |
| 8,831,305 | B2 | 9/2014 | Zhang |
| 8,837,669 | B2 | 9/2014 | Morton |
| 8,837,670 | B2 | 9/2014 | Akery |
| 8,840,303 | B2 | 9/2014 | Morton |
| 8,842,808 | B2 | 9/2014 | Rothschild |
| 8,859,981 | B1 | 10/2014 | Stoian |
| 8,861,684 | B2 | 10/2014 | Al-Kofahi |
| 8,885,794 | B2 | 11/2014 | Morton |
| 8,908,831 | B2 | 12/2014 | Bendahan |
| 8,913,707 | B2 | 12/2014 | Kang |
| 8,929,509 | B2 | 1/2015 | Morton |
| 8,958,526 | B2 | 2/2015 | Morton |
| 8,971,485 | B2 | 3/2015 | Morton |
| 8,971,487 | B2 | 3/2015 | Mastronardi |
| 8,983,033 | B2 | 3/2015 | Chen |
| 8,993,970 | B2 | 3/2015 | Morton |
| 9,001,973 | B2 | 4/2015 | Morton |
| 9,014,339 | B2 | 4/2015 | Grodzins |
| 9,020,095 | B2 | 4/2015 | Morton |
| 9,020,096 | B2 | 4/2015 | Allman |
| 9,020,103 | B2 | 4/2015 | Grodzins |
| 9,025,731 | B2 | 5/2015 | Kotowski |
| 9,036,779 | B2 | 5/2015 | Morton |
| 9,037,342 | B2 | 5/2015 | Shi |
| 9,042,511 | B2 | 5/2015 | Peschmann |
| 9,046,465 | B2 | 6/2015 | Thompson |
| 9,046,613 | B2 | 6/2015 | Ramsden |
| 9,048,061 | B2 | 6/2015 | Morton |
| 9,052,271 | B2 | 6/2015 | Grodzins |
| 9,052,403 | B2 | 6/2015 | Morton |
| 9,057,679 | B2 | 6/2015 | Morton |
| 9,081,099 | B2 | 7/2015 | Kang |
| 9,086,497 | B2 | 7/2015 | Bendahan |
| 9,093,245 | B2 | 7/2015 | Morton |
| 9,099,279 | B2 | 8/2015 | Rommel |
| 9,111,331 | B2 | 8/2015 | Parikh |
| 9,113,839 | B2 | 8/2015 | Morton |
| 9,117,564 | B2 | 8/2015 | Rommel |
| 9,121,958 | B2 | 9/2015 | Morton |
| 9,128,200 | B2 | 9/2015 | Muenster |
| 9,146,201 | B2 | 9/2015 | Schubert |
| 9,158,027 | B2 | 10/2015 | Morton |
| 9,158,030 | B2 | 10/2015 | Morton |
| 9,182,515 | B2 | 11/2015 | Stoian |
| 9,183,647 | B2 | 11/2015 | Morton |
| 9,208,988 | B2 | 12/2015 | Morton |
| 9,218,933 | B2 | 12/2015 | Langeveld |
| 9,223,049 | B2 | 12/2015 | Kotowski |
| 9,223,050 | B2 | 12/2015 | Kaval |
| 9,223,052 | B2 | 12/2015 | Morton |
| 9,257,208 | B2 | 2/2016 | Rommel |
| 9,263,225 | B2 | 2/2016 | Morton |
| 9,268,027 | B2 | 2/2016 | Kang |
| 9,268,044 | B2 | 2/2016 | Ramsden |
| 9,268,058 | B2 | 2/2016 | Peschmann |
| 9,274,065 | B2 | 3/2016 | Morton |
| 9,279,901 | B2 | 3/2016 | Akery |
| 9,285,488 | B2 | 3/2016 | Arodzero |
| 9,285,498 | B2 | 3/2016 | Carver |
| 9,291,582 | B2 | 3/2016 | Grodzins |
| 9,310,322 | B2 | 4/2016 | Panesar |
| 9,310,323 | B2 | 4/2016 | Bendahan |
| 9,316,760 | B2 | 4/2016 | Bendahan |
| 9,329,285 | B2 | 5/2016 | Gozani |
| 9,332,624 | B2 | 5/2016 | Morton |
| 9,417,060 | B1 | 8/2016 | Schubert |
| 9,420,677 | B2 | 8/2016 | Morton |
| 9,442,082 | B2 | 9/2016 | Morton |
| 9,465,119 | B2 | 10/2016 | Manslow |
| 9,466,456 | B2 | 10/2016 | Rommel |
| 9,535,019 | B1 | 1/2017 | Rothschild |
| 9,535,177 | B2 | 1/2017 | Ramsden |
| 9,541,510 | B2 | 1/2017 | Arodzero |
| 9,568,637 | B2 | 2/2017 | Stoian |
| 9,576,766 | B2 | 2/2017 | Morton |
| 9,606,259 | B2 | 3/2017 | Morton |
| 9,618,648 | B2 | 4/2017 | Morton |
| 9,638,646 | B2 | 5/2017 | Morton |
| 9,658,343 | B2 | 5/2017 | Arodzero |
| 9,675,306 | B2 | 6/2017 | Morton |
| 9,688,517 | B2 | 6/2017 | Morton |
| 9,714,920 | B2 | 7/2017 | Lionheart |
| 9,720,111 | B2 | 8/2017 | Ramsden |
| 9,726,619 | B2 | 8/2017 | Thompson |
| 9,726,766 | B2 * | 8/2017 | Neuer ...................... G01T 1/17 |
| 9,747,678 | B2 | 8/2017 | Chen |
| 9,747,705 | B2 | 8/2017 | Morton |
| 9,817,151 | B2 | 11/2017 | Morton |
| 9,880,315 | B2 | 1/2018 | Stoian |
| 9,958,569 | B2 | 5/2018 | Morton |
| 10,007,019 | B2 | 6/2018 | Morton |
| 10,032,021 | B2 | 7/2018 | Pedersen |
| 10,067,247 | B2 * | 9/2018 | Corre ...................... G01T 1/362 |
| 10,107,783 | B2 | 10/2018 | Lionheart |
| 10,126,442 | B2 | 11/2018 | Ramsden |
| 10,175,381 | B2 | 1/2019 | Morton |
| 10,228,487 | B2 | 3/2019 | Mastronardi |
| 10,274,636 | B2 | 4/2019 | Tang |
| 10,295,483 | B2 | 5/2019 | Morton |
| 10,302,807 | B2 | 5/2019 | Yu |
| 10,310,102 | B2 | 6/2019 | Ramsden |
| 10,317,566 | B2 | 6/2019 | Morton |
| 10,351,967 | B2 | 7/2019 | Wang |
| 10,388,818 | B2 | 8/2019 | Zhang |
| 10,393,915 | B2 | 8/2019 | Gozani |
| 10,408,967 | B2 | 9/2019 | Morton |
| 10,429,523 | B2 | 10/2019 | Ramsden |
| 10,473,795 | B2 | 11/2019 | Wang |
| 10,483,077 | B2 | 11/2019 | Morton |
| 10,585,207 | B2 | 3/2020 | Morton |
| 10,586,324 | B2 | 3/2020 | Zhao |

(56) References Cited

U.S. PATENT DOCUMENTS

| | | | |
|---|---|---|---|
| 10,591,424 B2 | 3/2020 | Morton | |
| 10,646,179 B2 | 5/2020 | Xu | |
| 10,663,413 B2 | 5/2020 | Li | |
| 10,663,616 B2 | 5/2020 | Morton | |
| 10,677,943 B2 | 6/2020 | Moore | |
| 10,739,491 B2 | 8/2020 | Yang | |
| 10,775,320 B2 | 9/2020 | Li | |
| 10,826,606 B1 | 11/2020 | Lundberg | |
| 10,901,112 B2 | 1/2021 | Morton | |
| 10,976,271 B2 | 4/2021 | Morton | |
| 2002/0094064 A1 | 7/2002 | Zhou | |
| 2003/0043964 A1 | 3/2003 | Sorenson | |
| 2003/0068557 A1 | 4/2003 | Kumashiro | |
| 2004/0017888 A1 | 1/2004 | Seppi | |
| 2004/0051265 A1 | 3/2004 | Nadeau | |
| 2004/0086078 A1 | 5/2004 | Adams | |
| 2004/0120454 A1 | 6/2004 | Ellenbogen | |
| 2004/0125914 A1 | 7/2004 | Kang | |
| 2004/0141584 A1 | 7/2004 | Bernardi | |
| 2004/0178339 A1 | 9/2004 | Gentile | |
| 2004/0252024 A1 | 12/2004 | Huey | |
| 2004/0258198 A1 | 12/2004 | Carver | |
| 2005/0023479 A1 | 2/2005 | Grodzins | |
| 2005/0024199 A1 | 2/2005 | Huey | |
| 2005/0100135 A1 | 5/2005 | Lowman | |
| 2005/0117683 A1 | 6/2005 | Mishin | |
| 2005/0117700 A1 | 6/2005 | Peschmann | |
| 2005/0135668 A1 | 6/2005 | Polichar | |
| 2005/0156734 A1 | 7/2005 | Zerwekh | |
| 2005/0157842 A1 | 7/2005 | Agrawal | |
| 2005/0161611 A1 | 7/2005 | Disdier | |
| 2005/0169421 A1 | 8/2005 | Muenchau | |
| 2005/0198226 A1 | 9/2005 | DeLia | |
| 2005/0275545 A1 | 12/2005 | Alioto | |
| 2006/0027751 A1 | 2/2006 | Kurita | |
| 2006/0056584 A1 | 3/2006 | Allman | |
| 2006/0114477 A1 | 6/2006 | Cox | |
| 2006/0140341 A1 | 6/2006 | Carver | |
| 2006/0182221 A1 | 8/2006 | Bernhardt | |
| 2006/0249685 A1 | 11/2006 | Tanaka | |
| 2006/0257005 A1 | 11/2006 | Bergeron | |
| 2006/0284094 A1 | 12/2006 | Inbar | |
| 2007/0085010 A1 | 4/2007 | Letant | |
| 2007/0110215 A1 | 5/2007 | Hu | |
| 2007/0140423 A1 | 6/2007 | Foland | |
| 2007/0172129 A1 | 7/2007 | Tortora | |
| 2007/0189454 A1 | 8/2007 | Georgeson | |
| 2007/0210255 A1 | 9/2007 | Bjorkholm | |
| 2007/0211248 A1* | 9/2007 | Caulfield | G06F 18/00 |
| | | | 356/301 |
| 2007/0228284 A1 | 10/2007 | Polichar | |
| 2007/0237293 A1 | 10/2007 | Singh | |
| 2007/0269005 A1 | 11/2007 | Chalmers | |
| 2007/0272874 A1 | 11/2007 | Grodzins | |
| 2007/0280416 A1 | 12/2007 | Bendahan | |
| 2007/0280502 A1 | 12/2007 | Paresi | |
| 2007/0286337 A1 | 12/2007 | Wang | |
| 2008/0037707 A1 | 2/2008 | Rothschild | |
| 2008/0044801 A1 | 2/2008 | Modica | |
| 2008/0048872 A1 | 2/2008 | Frank | |
| 2008/0084963 A1 | 4/2008 | Clayton | |
| 2008/0128624 A1 | 6/2008 | Cooke | |
| 2008/0159591 A1 | 7/2008 | Ruedin | |
| 2008/0170670 A1 | 7/2008 | Bhatt | |
| 2008/0198970 A1 | 8/2008 | Kirshner | |
| 2008/0205594 A1 | 8/2008 | Bjorkholm | |
| 2008/0230709 A1 | 9/2008 | Tkaczyk | |
| 2008/0260097 A1 | 10/2008 | Anwar | |
| 2008/0304622 A1 | 12/2008 | Morton | |
| 2009/0067575 A1 | 3/2009 | Seppi | |
| 2009/0086907 A1 | 4/2009 | Smith | |
| 2009/0116617 A1 | 5/2009 | Mastronardi | |
| 2009/0127459 A1 | 5/2009 | Neustadter | |
| 2009/0140158 A1 | 6/2009 | Clothier | |
| 2009/0168964 A1 | 7/2009 | Safai | |

| | | | |
|---|---|---|---|
| 2009/0200480 A1 | 8/2009 | Clothier | |
| 2009/0238336 A1 | 9/2009 | Akery | |
| 2009/0245462 A1 | 10/2009 | Agrawal | |
| 2009/0257555 A1 | 10/2009 | Chalmers | |
| 2009/0285353 A1 | 11/2009 | Ellenbogen | |
| 2009/0316851 A1 | 12/2009 | Oosaka | |
| 2010/0020937 A1 | 1/2010 | Hautmann | |
| 2010/0161504 A1 | 6/2010 | Casey | |
| 2010/0177868 A1 | 7/2010 | Smith | |
| 2010/0177873 A1 | 7/2010 | Chen | |
| 2010/0295689 A1 | 11/2010 | Armistead, Jr. | |
| 2011/0019797 A1 | 1/2011 | Morton | |
| 2011/0019799 A1 | 1/2011 | Shedlock | |
| 2011/0038453 A1 | 2/2011 | Morton | |
| 2011/0064192 A1 | 3/2011 | Morton | |
| 2011/0075808 A1 | 3/2011 | Rothschild | |
| 2011/0204243 A1 | 8/2011 | Bendahan | |
| 2011/0235777 A1 | 9/2011 | Gozani | |
| 2011/0266643 A1 | 11/2011 | Engelmann | |
| 2012/0099710 A1 | 4/2012 | Kotowski | |
| 2012/0104276 A1 | 5/2012 | Miller | |
| 2012/0116720 A1 | 5/2012 | Klann | |
| 2013/0001048 A1 | 1/2013 | Panesar | |
| 2014/0185771 A1 | 7/2014 | Morton | |
| 2014/0197321 A1 | 7/2014 | Bendahan | |
| 2014/0367582 A1* | 12/2014 | Boardman | G01T 1/16 |
| | | | 250/395 |
| 2015/0036798 A1 | 2/2015 | Morton | |
| 2015/0078519 A1 | 3/2015 | Morton | |
| 2015/0301220 A1 | 10/2015 | Morton | |
| 2015/0355117 A1 | 12/2015 | Morton | |
| 2015/0355369 A1 | 12/2015 | Morton | |
| 2016/0025889 A1 | 1/2016 | Morton | |
| 2016/0033674 A1 | 2/2016 | Allman | |
| 2019/0005598 A1* | 1/2019 | Hansell | B64C 39/024 |
| 2020/0116879 A1* | 4/2020 | Pavlovski | G06N 3/09 |
| 2020/0309972 A1* | 10/2020 | Price | G01T 1/2964 |

FOREIGN PATENT DOCUMENTS

| | | | |
|---|---|---|---|
| AU | 2008267661 B2 | 4/2011 | |
| AU | 2008267660 B2 | 6/2011 | |
| AU | 2014299147 B2 | 10/2016 | |
| CA | 2481596 C | 11/2009 | |
| EP | 0077018 A1 | 4/1983 | |
| EP | 0176314 | 4/1986 | |
| EP | 0287707 | 10/1988 | |
| EP | 0919186 A2 | 6/1999 | |
| EP | 1413898 A1 | 4/2004 | |
| EP | 1739460 A2 | 1/2007 | |
| EP | 1328827 B1 | 8/2008 | |
| EP | 2102636 B1 | 4/2012 | |
| EP | 2019974 B1 | 8/2013 | |
| EP | 2593813 B1 | 4/2014 | |
| EP | 2075595 B1 | 4/2015 | |
| EP | 2047293 B1 | 5/2015 | |
| EP | 2705386 B1 | 9/2015 | |
| EP | 2113791 B1 | 8/2016 | |
| EP | 2883085 B1 | 8/2018 | |
| EP | 1749220 B1 | 10/2019 | |
| EP | 2287636 B1 | 10/2019 | |
| EP | 3077852 B1 | 12/2019 | |
| EP | 2778716 B1 | 4/2020 | |
| EP | 3474292 B1 | 9/2020 | |
| EP | 3505975 B1 | 1/2021 | |
| GB | 2255634 A | 11/1992 | |
| GB | 2409268 A | 6/2005 | |
| GB | 2401766 B | 3/2006 | |
| GB | 2424065 A | 9/2006 | |
| GB | 2418015 B | 12/2006 | |
| GB | 2438317 A | 11/2007 | |
| GB | 2445578 B | 1/2009 | |
| GB | 2440588 B | 9/2009 | |
| GB | 2432094 B | 4/2010 | |
| GB | 2463254 B | 7/2010 | |
| GB | 2437979 B | 12/2010 | |
| GB | 2463707 B | 6/2011 | |
| GB | 2472420 B | 2/2012 | |
| GB | 2455906 B | 6/2012 | |

(56) References Cited

FOREIGN PATENT DOCUMENTS

| GB | 2490513 B | 11/2015 |
| GB | 2499391 B | 11/2015 |
| GB | 2504771 B | 2/2016 |
| GB | 2522017 B | 9/2017 |
| GB | 2520762 B | 4/2018 |
| GB | 2525826 B | 9/2020 |
| GB | 2555564 B | 9/2020 |
| GB | 2560552 B | 9/2020 |
| GB | 2577909 B | 11/2020 |
| GB | 2552538 B | 12/2020 |
| WO | 1998055851 A1 | 12/1998 |
| WO | 2004010127 A1 | 1/2004 |
| WO | 2004109331 | 12/2004 |
| WO | 2005098400 | 10/2005 |
| WO | 2006036076 A1 | 4/2006 |
| WO | 2006045019 | 4/2006 |
| WO | 2006053279 A2 | 5/2006 |
| WO | 2006078691 A2 | 7/2006 |
| WO | 2006095188 | 9/2006 |
| WO | 2007035359 A2 | 3/2007 |
| WO | 2007051092 A2 | 5/2007 |
| WO | 2007055720 A2 | 5/2007 |
| WO | 2007068933 A1 | 6/2007 |
| WO | 2007103216 A2 | 9/2007 |
| WO | 2008017983 | 2/2008 |
| WO | 2009106803 A2 | 9/2009 |
| WO | 2009141613 | 11/2009 |
| WO | 2009141615 | 11/2009 |
| WO | 2009143169 A1 | 11/2009 |
| WO | 2009150416 A2 | 12/2009 |
| WO | 2011069024 A1 | 6/2011 |
| WO | 2011087861 A2 | 7/2011 |
| WO | 2011091070 A2 | 7/2011 |
| WO | 2013116549 A1 | 8/2013 |
| WO | 2013119423 A1 | 8/2013 |
| WO | 2014107675 | 7/2014 |
| WO | 2014121097 A1 | 8/2014 |
| WO | 2014124152 A2 | 8/2014 |
| WO | 2016011205 | 1/2016 |

OTHER PUBLICATIONS

Molchanov P A et al: 'Nanosecond gated optical sensors for ocean optic applications' Sensors Applications Symposium, 2006. Proceedings of The 2006 IEEE Houston, Texas, USA Feb. 7-9, 2006, Piscataway, NJ, USA, IEEE, Feb. 7, 2006 (Feb. 7, 2006) , pp. 147-150, XP010917671 ISBN: 978-0-7803-9580-0.
International Search Report PCT/GB2009/000515, Feb. 23, 2010, Rapiscan Security Products, Inc.
International Search Report for PCT/GB2009/000497, Jan. 22, 2010.
International Search Report PCT/GB2009/001444, Apr. 6, 2010, Rapiscan Security Products.
International Search Report for PCT/GB2009/000556, Feb. 19, 2010, Rapiscan Security Products, Inc.
International Search Report for PCT/GB2009/001277, Jul. 20, 2010, Rapiscan Systems Inc.
International Search Report for PCT/GB2009/001275, Jul. 24, 2009, Rapiscan Security Products Inc.
International Search Report for PCT/GB2009/001250, Mar. 2, 2010, Rapiscan Security Products Inc.
International Search Report for PCT/US2010/061908, mailed on Apr. 2, 2012, Rapiscan Systems, Inc.
International Search Report for PCT/GB2006/000859, mailed on May 19, 2006, Corus UK Ltd.
Misso et al., "New developments in radiation detectors and electron multipliers", 1964, IEEE Transactions on Nuclear Science pp. 72-75.
International Search Report for PCT/US23/71427, Jan. 3, 2024.
CRS Report for Congress, Aviation Security Technologies and Procedures: Screening Passengers and Baggage, Oct. 26, 2001, pp. 1-12.
International Search Report for PCT/US2015/040653, Dec. 16, 2015.
International Search Report for PCT/US14/56652, Apr. 27, 2015.
International Search Report for PCT/US14/14198, May 16, 2014.
International Preliminary Report on Patentability for PCT/US2014/014198, Aug. 4, 2015.
International Search Report for PCT/US11/21758; Jul. 7, 2011, Rapiscan Systems Inc.
International Preliminary Report on Patentability for PCT/US11/21758, Jul. 7, 2011.
Written Opinion on Patentability for PCT/US11/21758; Jul. 7, 2011; Rapiscan Systems.
International Search Report for PCT/GB09/00575, Apr. 7, 2010.
Smith C. R. et al: 'Application of 450 kV computed tomography to engine blocks with steel liners' Materials Evaluation vol. 65, No. 5, 2007, pp. 458-461, XP055108238.
International Search Report for PCT/US13/23676, Jun. 28, 2013.
International Search Report for PCT/US13/24191, Rapiscan Systems Inc., mailed on Jun. 25, 2013.
International Search Report for PCT/US2014/010370, May 13, 2014.
International Search Report for PCT/US10/58809; Rapiscan Systems Inc.; Apr. 19, 2011.
International Search Report for PCT/US2014/015126, May 27, 2014.
Written Opinion of the International Searching Authority for PCT/US2014/015126, May 27, 2014.
International Search Report for PCT/US2012/054110, Dec. 24, 2012.

* cited by examiner

1200

1201

1202

1203

1204

1205

120n

302 — A database of training spectra is generated

304 — Energy spectra radiated by an object being inspected in a radiation inspection system is gathered 306 — The gathered energy spectra is normalized by using one or more predefined normalization techniques 308 — The normalized spectra are energy scaled 310 — The normalized and scaled spectra is fitted to each of the training spectra in the database 312 — A residual of fitting the normalized scaled spectra with respect to each of the training spectra classes is determined 314 — The normalized scaled spectra is identified as belonging to the class of training spectra that results in the smallest residual

FIG. 3A

SYSTEMS AND METHODS FOR CLASSIFICATION OF RADIATION ENERGY SPECTRA

CROSS-REFERENCE

The present specification relies on U.S. Patent Provisional Application No. 63/374,272, titled "Systems and Methods for Classification of Radiation Energy Spectra", and filed on Sep. 1, 2022, for priority. The above-mentioned application is herein incorporated by reference in its entirety.

FIELD

Embodiments of the present specification relate to the field of radiation-based inspection systems. Specifically, embodiments of the present specification relate to systems and methods for material discrimination based on real-time classification of detected energy spectra generated from radiation-based inspection systems.

BACKGROUND

Trade fraud, smuggling, and terrorism have increased the need for non-intrusive inspection systems such as X-ray, gamma ray, and linear accelerator (LINAC)-based systems for inspecting cargo, trucks, passenger vehicles, and other transportation systems, which efficiently provide for the movement of commodities across borders. In addition, they provide opportunities for the inclusion of contraband items such as weapons, explosives, illicit drugs and precious metals. In particular, non-intrusive inspection systems are used in applications ranging from curbside inspection of parked vehicles to scanning in congested or high traffic ports. The term port while generally accepted as referring to a seaport, also applies to a land border crossing or any port of entry.

A radiation portal monitor (RPM) is a passive system used to detect the presence of ionizing radiation sources passing through it, typically for security of borders or ports of entry. These systems are used for scanning vehicles, cargo containers, rail cars, and pedestrians. In addition, similar systems are used for inspection of scrap metal at steel recycling plants, where it is possible that a radioactive source is melted and accidentally mixed in with the scrap steel, representing a large cost by contamination of a multi-million-dollar crucible.

Naturally occurring radiation materials (NORM) may cause these systems to alarm which requires the operators of the system to halt traffic in order to investigate the cause of the alarm. NORM sources comprise isotopes such as Ra-226, Th-232/Tl-208, K-40, and U-238. While the presence of a NORM source is usually acceptable for these applications, they represent a "nuisance" alarm. The goal for these systems is to try to reduce these NORM nuisance alarms as much as possible to levels below 1%, as NORM sources are the cause of most nuisance alarms from radiation portals.

Conventionally, reduction of nuisance alarms due to presence of NORM substances requires use of costly detectors that offer increased energy resolution in order to identify the specific NORM isotopes causing alarms. The high energy resolution detectors are used to determine specific energy peaks within a detected spectrum that are caused due to NORM isotopes. Hence, the method uses very specific portions of the detected energy spectrum to determine the presence of a NORM source. Other known methods of reducing nuisance alarms due to the presence of NORM substances require the use of algorithms for carrying out clustering/binning of similar energy radiation and then applying decisions for sounding alarms on said clustered radiation based on ratios of the counts in these energy bins to try and conclude the alarm was attributed to a NORM source. Even with automated systems, it becomes difficult to comply with the implied requirement to keep the number of false alarms low, when the system is operated at high throughputs.

Hence, there is need for a system and method for reducing nuisance alarms in radiation-based inspection portals. There is also a need for a system and method that uses low cost detectors, and performs analysis of a detected radiation spectrum in its entirety in a machine learning framework, for determining whether the alarm is caused by a NORM material.

SUMMARY

The following embodiments and aspects thereof are described and illustrated in conjunction with systems, tools and methods, which are meant to be exemplary and illustrative, and not limiting in scope. The present application discloses numerous embodiments.

The present specification discloses a radiation portal monitor comprising a plurality of detectors in data communication with a processing system wherein the processing system is configured to determine if a radiation spectrum comprises radiation corresponding to naturally occurring radiation material sources (NORM) by: generating a database of training spectra, each of the training spectra in the database representing a NORM material; gathering the radiation spectra; normalizing the gathered spectra by using one or more predefined normalization techniques; energy scaling the normalized spectra by using one or more energy scaling techniques; fitting the normalized and scaled spectra to each of the training spectra in the database; determining a residual of fitting the normalized and scaled spectra with respect to each of the training spectra; and identifying the normalized and scaled spectra as a NORM material based on the residual and a threshold value.

Optionally, the normalized and scaled spectra is determined as a NORM material if the residual is less than the threshold value.

Optionally, the processor is further configured to identify the normalized scaled spectra as belonging to an 'other' category if the residual is greater than the threshold value.

Optionally, the processor is configured to determine the threshold value empirically based on the training spectra and the residual of fitting the normalized scaled spectra with a class of the training spectra.

Optionally, gathering radiation spectra comprises gathering energy spectra radiated by an object being inspected in a radiation portal monitor by using one or more of the plurality of detectors. Optionally, the plurality of detectors are large-area low-resolution radiation detectors. Optionally, the radiation detectors are polyvinyltoluene (PVT) detectors. Optionally, the radiation detectors are gamma radiation detectors. Optionally, the radiation portal monitor is a passive system that does not include a radiation source. Optionally, the radiation portal monitor is a passive radiation portal monitor (RPM) used to detect presence of ionizing radiation sources passing through the RPM. Optionally, the RPM comprises a plurality of panels, wherein the panels are spaced so to enable a cargo container to pass between two panels. Optionally, each of the panels comprises a radiation detector.

Optionally, energy scaling the normalized spectra comprises applying predefined weights to the gathered energy spectra to obtain a weighted matrix of said spectra.

Optionally, the one or more energy scaling techniques comprise the Spectrum Dose Index (SDI) technique. Optionally, the SDI technique adds more weight to higher energies in the normalized spectra for aiding in determination of NORM materials.

Optionally, the one or more training spectra used to train Optimal Linear Associative Memory (OLAM) based artificial neural networks is used to populate the database of training spectra. Optionally, the training spectra for an OLAM based artificial neural network comprises one spectrum from each isotope of NORM materials.

Optionally, an Optimal Linear Associative Memory (OLAM) neural network implemented within a field-programmable gate array (FPGA) integrated circuit is used to determine if the radiation spectra comprises radiation corresponding to NORM materials.

Optionally, the normalized and scaled spectra is fitted to each of the training spectra in the database in a sequential fashion.

Optionally, the NORM materials are one of: Ra-226, Th-232/Tl-208, K-40, and U-238.

In some embodiments, the present specification discloses a method of determining if radiation spectra comprises radiation corresponding to naturally occurring radiation material sources (NORM), the method comprising: generating a database of training spectra, each of the training spectra in the database representing a NORM material; gathering the radiation spectra; normalizing the gathered spectra by using one or more predefined normalization techniques; energy scaling the normalized spectra by using one or more energy scaling techniques; fitting the normalized and scaled spectra to each of the training spectra in the database; determining a residual of fitting the normalized scaled spectra with respect to each of the training spectra classes; and identifying the normalized scaled spectra as a NORM material based on the residual of fitting the normalized scaled spectra with a class of the training spectra and a threshold value.

Optionally, the normalized scaled spectra is determined as a NORM material if the residual of fitting the normalized scaled spectra with a class of the training spectra is less than the threshold value.

Optionally, the method further comprises identifying the normalized scaled spectra as belonging to an 'other' category if the residual of fitting the normalized scaled spectra with a class of the training spectra is greater than the threshold value.

Optionally, the threshold value is determined empirically based on the training spectra in the database and the residual of fitting the normalized scaled spectra with a class of the training spectra.

Optionally, gathering radiation spectra comprises gathering energy spectra radiated by an object being inspected in a radiation inspection system by using one or more radiation detectors.

Optionally, the radiation detectors are large-area low-resolution detectors. Still optionally, the radiation detectors are polyvinyltoluene (PVT) detectors. Still optionally, the radiation detectors are gamma radiation detectors.

Optionally, the radiation inspection system is a passive system that does not include a radiation source. Still optionally, the radiation inspection system is a passive radiation portal monitor (RPM) used to detect presence of ionizing radiation sources passing through the RPM. Optionally, the RPM comprises a plurality of panels, wherein the panels are spaced so to enable a cargo container to pass between two panels. Optionally, each of the panels comprises a radiation detector.

Optionally, energy scaling the normalized spectra comprises applying predefined weights to the gathered energy spectra to obtain a weighted matrix of said spectra.

Optionally, the one or more energy scaling techniques comprise the Spectrum Dose Index (SDI) technique. Still optionally, the SDI technique adds more weight to higher energies in the normalized spectra for aiding in determination of NORM materials.

Optionally, one or more training sets used to train an OLAM based artificial neural networks is used to populate the database of training spectra.

Optionally, the Optimal Linear Associative Memory (OLAM) neural network implemented within a field-programmable gate array (FPGA) integrated circuit is used to determine if the radiation spectra comprises radiation corresponding to NORM materials.

Optionally, the training spectra for an OLAM based artificial neural network comprises one spectrum from each isotope of NORM materials.

Optionally, the normalized and scaled spectra is fitted to each of the training spectra in the database in a sequential fashion.

Optionally, the NORM materials are one of: Ra-226, Th-232/Tl-208, K-40, and U-238.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g. boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 3A is a flow chart illustrating a method of classifying energy spectra, in accordance with an embodiment of the present specification;

DETAILED DESCRIPTION

Figure 1A:
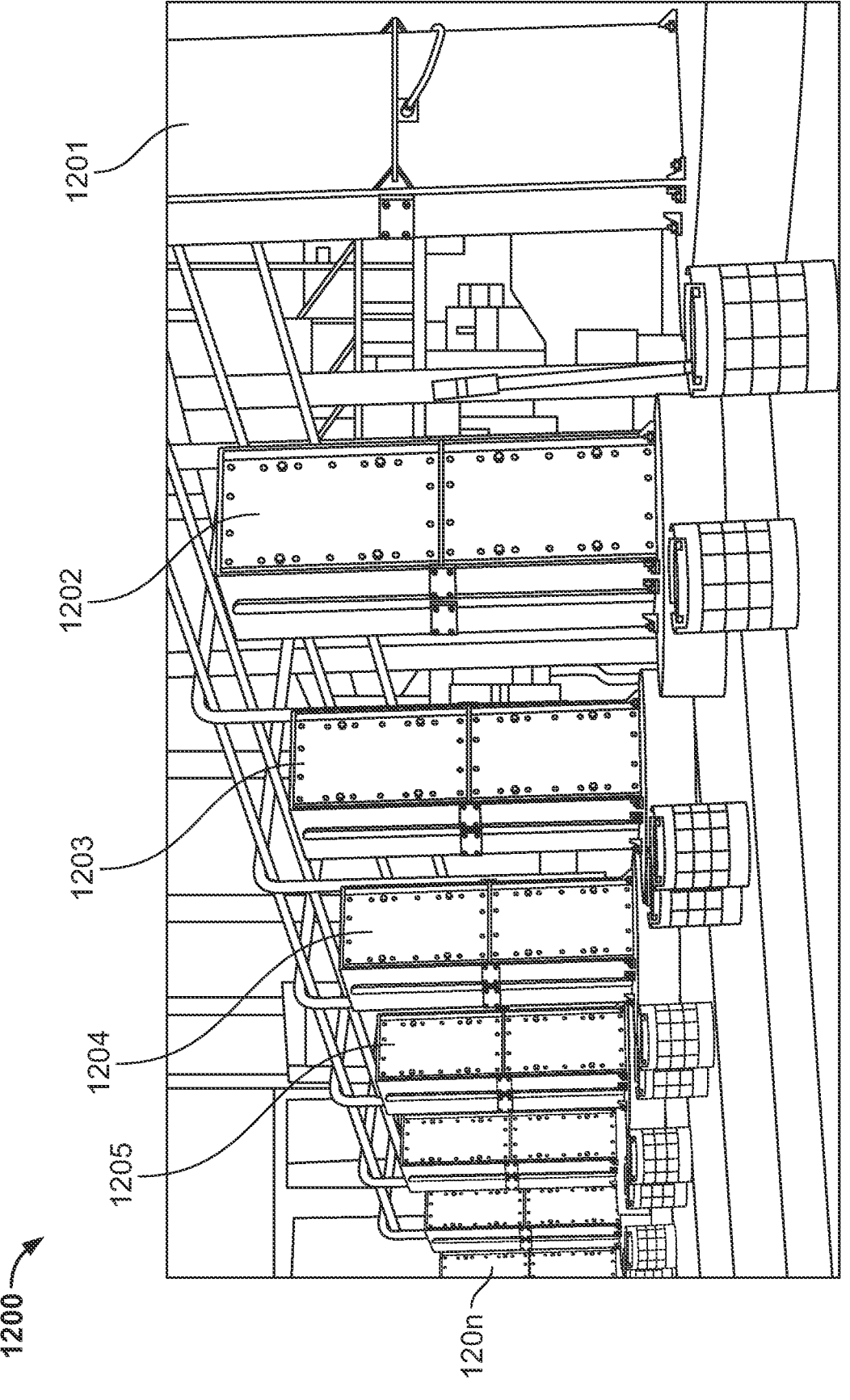
FIG. 1A illustrates an exemplary inspection system comprising a plurality of radiation portal monitors (RPMs), in which the system and method of the present specification may be employed.

In embodiments, the present specification provides a system and method for reducing false alarms in radiation-based inspection systems. In embodiments, the system and method of the present specification provide a quick real-time classification of detected energy spectra from radiation-based inspection systems into naturally occurring radiation material sources (NORM), or 'other' categories and the percent match to each class. NORM sources comprise isotopes such as Ra-226. Th-232/Tl-208, K-40, and U-238.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

In various embodiments, the system includes at least one processor capable of processing programmatic instructions, has a memory capable of storing programmatic instructions, and employs software comprised of a plurality of programmatic instructions for performing the processes described herein.

In various embodiments, a computing device may be employed to receive and process data signals and image data and may include an input/output controller, at least one communication interface and a system memory. The system memory includes at least one random access memory (RAM) and at least one read-only memory (ROM). These elements are in communication with a central processing unit (CPU) to enable operation of the computing device. In various embodiments, the computing device may be a conventional standalone computer or alternatively, the functions of the computing device may be distributed across a network of multiple computer systems and architectures. In some embodiments, execution of a plurality of sequences of programmatic instructions or code, which are stored in one or more non-volatile memories, enable or cause the CPU of the computing device to perform or enable various functions, processes and algorithms, such as, for example, performing image reconstruction for display on a screen. In alternate embodiments, hard-wired circuitry may be used in place of, or in combination with, software instructions for implementation of the processes of systems and methods described in this application. Thus, the systems and methods described are not limited to any specific combination of hardware and software.

FIG. 1A illustrates an inspection system comprising a plurality of radiation portal monitors (RPMs), in accordance with an embodiment of the present specification. The radiation portal monitor 1200 depicted in FIG. 1A comprises a plurality of detector panels 1201, 1202, 1203, 1204, 1205 . . . 120*n*, wherein each detector panel comprises a plurality of radiation detectors. In embodiments, the panels 1201, 1202, 1203, 1204, 1205 . . . 120*n*, are spaced at a distance to enable a cargo vehicle to pass between two panels. In embodiments, the distance between the panels varies depending upon a size of the vehicle passing between the panels, and may be large enough to allow even the biggest dump trucks used in steel recycling plants to pass through. Thus, in embodiments, the distance may vary from 1 meter to 10*s* of meters. In other embodiments, the system may employ single detectors on either side without changing the operations/methods described herein.

Figure 1B:
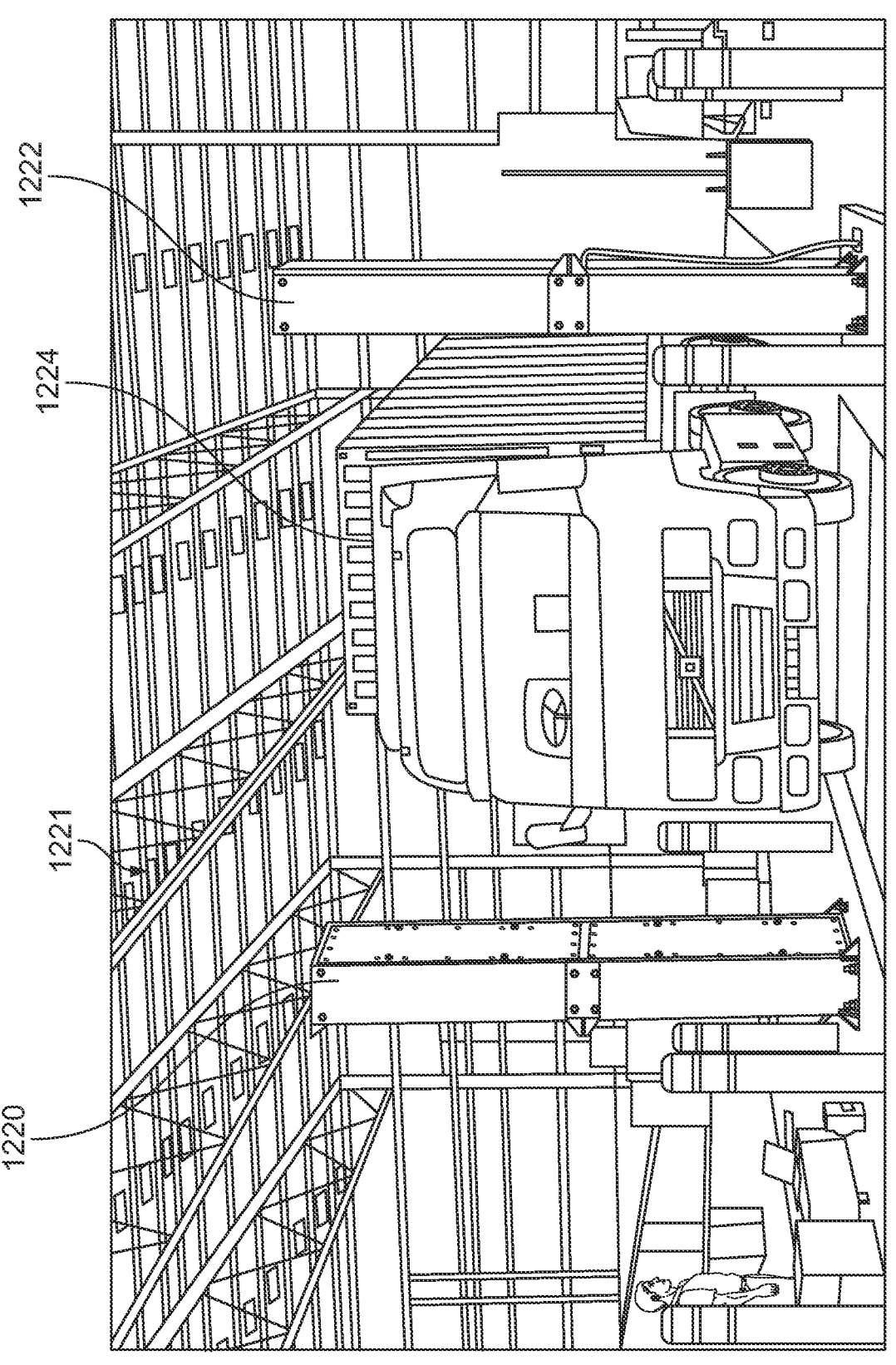
FIG. 1B illustrates a radiation portal monitor (RPM) being used to inspect cargo, in accordance with an embodiment of the present specification.

FIG. 1B illustrates a radiation portal monitor (RPM) for inspecting cargo, while in use, in accordance with an embodiment of the present specification. Referring to FIG. 1B, in embodiments, RPM 1221 includes a first panel 1220 and a second panel 1222 which comprise one or more detectors for detecting radiation scattered by a cargo 1224 driving through and between the first panel 1220 and second panel 1222, and a processor configured to process the detected radiation and provide information indicating whether the cargo comprises any radiation source materials. In embodiments, the RPM 1221 does not comprise any source of radiation, and the only radiation that is detected by the first panels 1220 and second panel 1222 is the radiation which emanates from the cargo 1224 passing through the system. Hence, in various embodiments, the inspection system of the present specification comprising a plurality of Radiation Portal Monitors (RPMs) having multiple detector panels is a passive system that does not generator or emit X-rays for imaging purposes, and operates only to detect radioactive materials that travel through the detector panels. The plurality of panels may comprise gamma and neutron detector materials such as Polyvinyltoluene (PVT) plastic scintillator and LiZnS-PMMA, respectively. In embodiments, the panels are capable of both gamma and neutron detection and can detect and identify radioactive nuclides. Such modular drive-through inspection systems may be configured to support the unique needs of the nuclear industry, law enforcement, private industry, research institutes, steel mills, scrap steel recycling plants and federal agencies tasked with nuclear safety or public security.

In an embodiment, the RPM 1221 may be used in conjunction with an active X-ray imaging system, particularly with application of blanking synchronization of the RPM system when X-rays are emitted. In an embodiment, the method of the present specification for suppressing nuisance alarms due to NORM materials may be implemented in RPM systems contained within an X-ray imaging system. U.S. Pat. No. 8,963,094 titled "Composite gamma-neutron detection system" and filed on Feb. 24, 2015 and U.S. Pat. No. 10,393,915, titled "Integrated primary and special nuclear material alarm resolution", and filed on Aug. 27, 2019, assigned to the Applicant of the present specification are herein incorporated by reference in their entirety.

The classification systems and methods of the present specification enables reduction of nuisance alarms in passive radiation portal monitors wherein the classification information may be used to determine whether to notify an operator of an alarm based on the presence of a potential radiation-based threat. In embodiments, the classification systems and methods of the present specification may be used to reduce nuisance alarms in any passive radiation detection system, such as, but not limited to, portals, conveyers, handhelds, scrap steel scanning systems, and area monitors that are configured to generate an alarm upon detection of gamma radiation and are used to measure energy spectra emanating from radioactive substances.

Figure 1C:
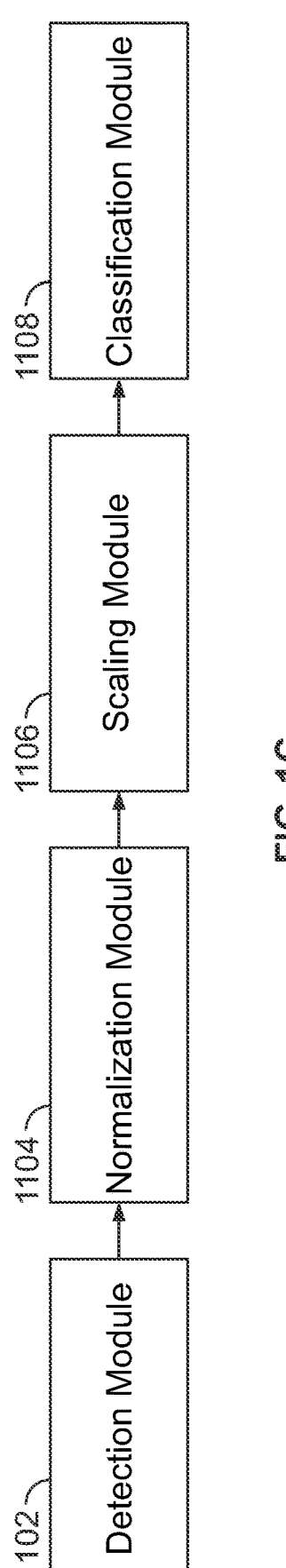
FIG. 1C illustrates a block diagram of a classification system, in accordance with an embodiment of the present specification.

FIG. 1C illustrates a block diagram of the classification system, in accordance with an embodiment of the present specification. The system 1100 comprises a detection module 1102, a normalization module 1104, a scaling module 1106 and a classification module 1108. Detection module 1102 comprises a plurality of radiation detectors for gathering energy spectra generated by an object under inspection in a radiation inspection system. In an embodiment the radiation comprises gamma rays. In an embodiment, the plurality of detectors are large-area low-resolution polyvinyltoluene (PVT) detectors which have poor resolution and are not well suited for isotope identification. In embodiments, conventional PVT detectors may be used without making any physical modifications to the detectors. In embodiments, the detection module 1102 comprises PVT detectors as they provide a large detection area and are available at a low cost. Further, PVT detectors may be programmed and calibrated/trained to implement the requirements of the classification module 1108 (described below) more easily as compared to high resolution detectors. In a preferred embodiment, the detection module 1102 comprises one or more PVT detectors. In other embodiments, detection module 1102 comprises any gamma ray detector, having high or low resolution that may be used for isotope identification.

Normalization module 1104 normalizes the gathered energy spectra by using one or more predefined normalization techniques, as further described below.

Scaling module 1106 uses at least one predefined technique to energy scale the normalized energy spectra. In an embodiment, but not limited to such embodiment, scaling module 1106 applies predefined weights to the gathered energy spectra to form a weighted matrix of said spectra by using a Spectrum Dose Index (SDI) technique, which helps to boost the high energy counts from isotopes that emit higher energy gamma radiation in the energy spectra. In embodiments, SDI is a simple scaling that is used to compensate for increases in detected gamma energy.

In an embodiment, the SDI technique comprises determining a number of counts in a channel of a histogram of the energy spectrum, multiplying the determined counts by the channel number, and summing up all of the multiplied counts. By way of background, as used in the specification, a channel corresponds to a physically defined region of a detector that generates a single electrical signal corresponding to the number of photons received at that physical location—also known as a "count"-over a predefined period of time. In embodiments, the scaling module 1106 enables scaling up of the higher energy isotopes from the object being irradiated by gamma rays, which may correspond to NORM sources. In embodiments, energy scaling causes the shape of the spectrum towards the higher energies to have more pronounced features. Energy scaling compensates for detector efficiency with respect to detector energy. As is known, a gamma ray detector becomes less efficient as the gamma energy increases. In embodiments, the efficiency of a detector is measured for a plurality of gamma energies and a resultant energy efficiency curve is used to boost low efficiency regions of the detector.

In embodiments, an x-axis of the histogram of energy spectrum depicts integer bins 'x', wherein x=1, 2, 3 . . . n, representing the amplitudes of the pulses collected from the gamma detector. The y-axis of the histogram of energy spectrum represents the quantity of events which occurred for each amplitude bin, and are depicted as a function of x (i.e. F(x)) where x ranges from 1 to n and F(x) ranges from 0 to the size of the variable chosen to represent these values (typically a 16-bit or 32-bit variable). In embodiments, the SDI scaling technique is used to scale the function F(x) by multiplying each F(x) by its bin number x, by using the formula:

$$SDI(x) = F(x) * x \text{ where } x = 1, 2, \ldots n. \quad \text{(Equation 1)}$$

Since the histogram of detector pulse amplitudes can be scaled so that the x-axis represents the gamma energy, and the energy response of gamma detectors becomes less efficient as the gamma energy increases, the SDI technique compensates for the decreased efficiency of the detector by boosting the number of events as the energy of detected rays increases. Thus, the use of the SDI technique adds more weight to higher energies in the spectrum which aid in determination of NORM sources. For example, if the efficiency of the detector is 20% at 2 MeV, then the counts received in the detector at this region are scaled up by dividing the counts received by 0.2.

Figure 2:
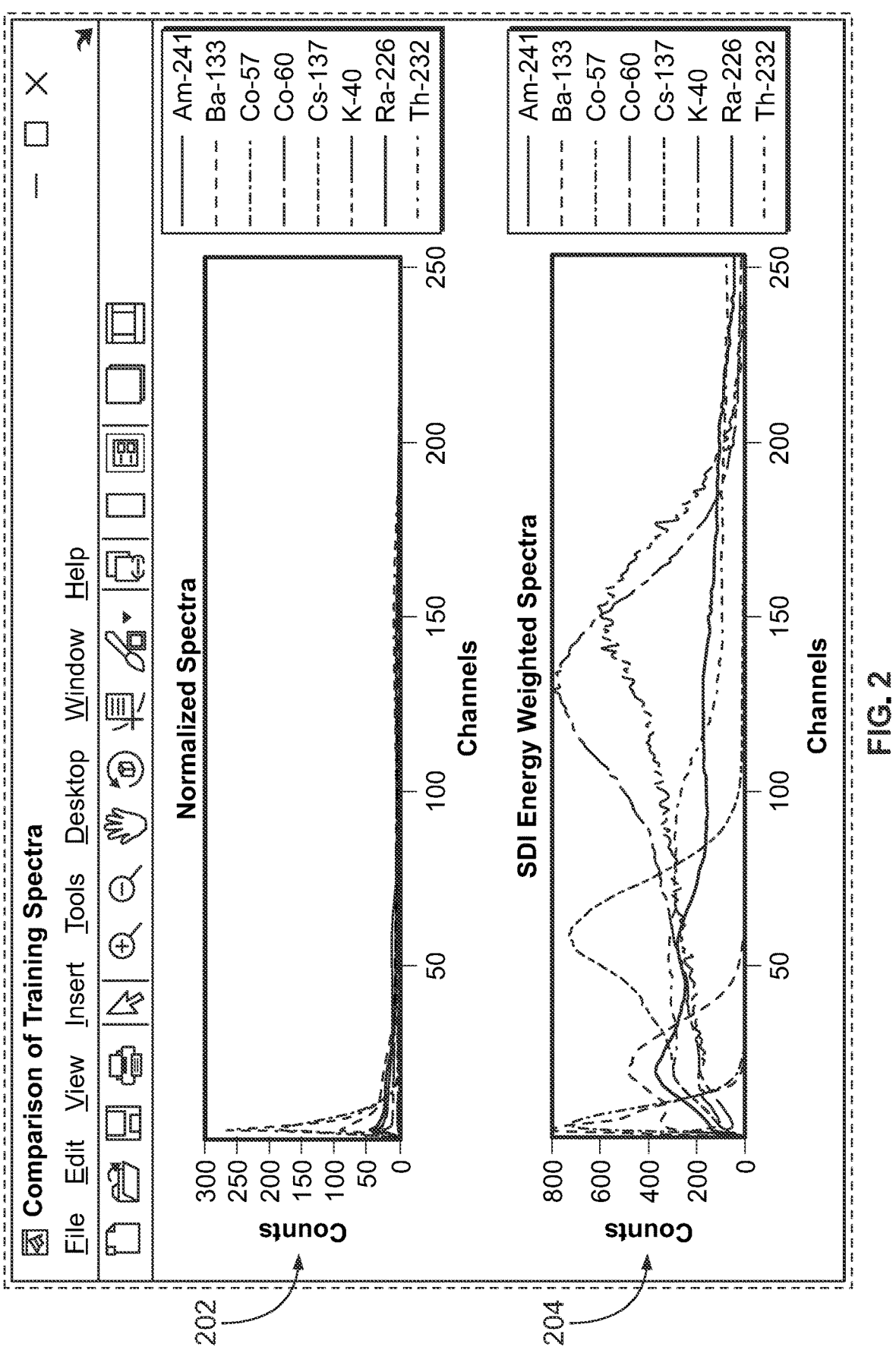
FIG. 2 depicts graphs of normalized and scaled energy weighted spectra, in accordance with an embodiment of the present specification.

FIG. 2 illustrates plots of normalized and scaled energy spectra, in accordance with an embodiment of the present specification. Plot 202 represents a normalized spectra before energy scaling is applied to said spectra. Plot 204 represents the energy spectra of plot 202 after said spectra has been energy scaled by application of one or more energy weighting techniques.

Referring to FIG. 1C, classification module 1108 determines the materials corresponding to each energy reading in the scaled energy spectra and classifies each energy reading into one or more predefined categories. In an embodiment, the classification module categorizes the energy spectra into 'NORM' or 'other' categories and identifies the percent match to each category. In embodiments, the 'other' category denotes all other materials/isotopes which are not NORM materials. Examples of NORM materials comprise, but are not limited to, radioactive isotopes of Potassium (K-40), Thorium (Th-232), Uranium (U-238), and Radium (Ra-226). In an embodiment, classification module 1108 uses an Optimal Linear Associative Memory (OLAM) based artificial neural network to categorize the energy scaled spectra for determining energy sources belonging to the NORM category. In an embodiment, other machine learning techniques such as, but not limited to, a k-NN (k nearest neighbor) network may be used to categorize the energy scaled spectra for determining energy sources belonging to the NORM category.

In various embodiments, in order to achieve the OLAM based implementation of the present specification, it is required that the gathered energy spectra are scaled to correspond to the training data and coefficients derived offline. Since the collected energy spectrum may contain more or less data than the predefined training data, the collected energy spectra must be re-scaled to a size corresponding to the training data in order to apply the training data coefficients to the collected energy spectra. In an embodiment, re-scaling is achieved by using mathematical operations such as multiplication or division. In embodiments, the gathered energy spectra include a plurality of energy bins comprising radiation of similar energies, wherein each energy bin is assigned a bin number. In embodiments, the energy bins are of a constant energy size such as, but not limited to, 3 keV per energy bin or "channel". The energy bins are formed by the analog-to-digital conversion of the pulse heights of pulses received from a radiation detector. For example, if the pulse heights have 10 bits of resolution, then 1024 energy bins are formed. These correspond to the voltage of the pulses received from the radiation detector, which are proportional to the current from the detector, which are, in turn, proportional to the energy deposited in the detector by the gamma photons that interact within the detector. In an embodiment, after calibration, the energy bins may be energy scaled to an energy level of 3 keV, for example, in the case of the radiation detector being a high-resolution detector. In embodiments, for a PVT detector, having a lower resolution, the pulse heights of pulses received from the detector may be of 8 bits of resolution which results in 256 energy bins being formed. If the bins are calibrated to cover 3 MeV (3000 keV) of energy, the energy bins may represent 3000 keV/256=11.7 keV energy per bin.

In an embodiment, once the collected energy spectrum has been re-scaled to a comparable size as the training data by applying multiplication or division to each bin of the energy spectrum, a coefficient array for each category (NORM or OTHER) is obtained by obtaining a dot product of an array of the training data and the collected normalized energy spectrum. The dot product is a sum of the bin-by-bin multiplication of the coefficient array and the energy spectrum. This embodiment requires intensive mathematical processing and hence is a less preferred embodiment.

In an embodiment, the normalization module is configured to enable implementation of Optimal Linear Associative Memory (OLAM) within a field-programmable gate array (FPGA) integrated circuit. In a preferred embodiment, the normalization module 1104 is configured to normalize the gathered energy spectra by counting the number of counts in the energy spectra collected into an energy histogram. In embodiments, a predefined number of counts are required to be collected for the classification module 1108. For example, if 1000 counts are required for making a classification decision, while determining coefficients for operation of the OLAM classifier offline, each class of the energy spectra is normalized to contain a total of 1000 counts. So, in case of an energy spectrum lasting for a duration of 10 minutes and comprising a million counts, each energy bin of the corresponding histogram is scaled so that the sum of all the energy bins equals 1000.

In embodiments, a coefficient is determined for each energy category from the normalized spectra using the OLAM algorithm. In embodiments, the coefficients for each category (NORM or OTHER) is accumulated per count until a total of a 1000 counts have occurred, which is when it is determined if the 1000 counts correspond a 'NORM' or 'OTHER' type of radiation source. As a count occurs, the amplitude of the count corresponds to the bin within the energy spectrum to which the count belongs, which is 1 while all other bins are 0. In an embodiment, the coefficient for that bin is added to an accumulator and once the number of counts reaches the predefined number of counts (in this example, 1000), the processing is completed and the accumulator for each energy class is used to determine a winning energy class, which is used to further determine if the energy class belongs a NORM or OTHER type of radiation source.

In an embodiment, the SDI technique comprises multiplying the number of counts in a particular energy bin by the bin number. For example, if there are two counts in an energy bin having a bin number of 200, then the SDI scaling method would include multiplying the two counts by 200 which is equal to 400. In an embodiment, a scaling technique comprising using an inverse of the energy efficiency curve of the detector is used to boost the energy bins having lower energy. For example, if the energy represented by bin number 200 is only 20% efficient, then this bin is scaled by dividing the counts within it by 0.2 in order to boost the energy efficiency of said energy bin. In other embodiments, various other suitable scaling techniques may be used to scale the gathered energy spectra, without limiting the scope of the present specification.

The classification module 1108 provides two categories, specifically 'NORM' and 'other', to an OLAM algorithm training set. As is known, when used for isotope identification, the OLAM algorithm always presents, as an answer, results in only one of the categories or isotopes present in the training sets used to train OLAM based artificial neural networks. Thus, the OLAM algorithm is capable of identifying only the one or more isotopes present in its training sets. If the OLAM network is trained by using each known NORM source and the fact that NORM sources typically have higher energy features than other sources of radiation, and if the trained OLAM network is presented with a new isotope that is not present in the training sets, then the OLAM algorithm does not recognize the new isotope and uses a least squares residual technique to classify said isotope as 'other' material by default. Hence if the OLAM algorithm does not recognize a particular energy spectrum obtained from the scaling module 1106, said energy spectrum is categorized as belonging to an 'other' isotope/material. In other embodiments, classification module 1108 uses various other classification techniques to categorize the energy spectra for identifying NORM isotopes. In other embodiments, other neural networks such as, but not limited to a k-NN (k nearest neighbor) network may be used to categorize the energy scaled spectra for determining energy sources belonging to the NORM category.

In embodiments, where the OLAM neural network is used to classify an unknown/gathered, energy scaled spectra into a 'NORM' or an 'other' class, the output of the OLAM algorithm is in the form of two numbers that correspond to the extent at which (how much) the unknown energy scaled spectra matches each of the two classes. For example, if the energy scaled spectra comprises a 'NORM' source, the output of the OLAM network is approximately 100% for the 'NORM' class and approximately 0% for the 'other' class. In another example, if a scaled energy spectrum comprises a mix of isotopes comprising Am-241 and Ba-133 (which belong to the 'other' class) and Ra-226 (which belongs to the 'NORM' class) and each isotope contributes approximately 33% to the total counts in the scaled energy spectrum, then the output of the OLAM network is approximately 66% for the 'other' class and 33% for the 'NORM' class.

FIG. 3A is a flow chart illustrating a method for classifying energy spectra, in accordance with an embodiment of the present specification. At step 302, a database of training spectra is generated. In an embodiment, one or more training sets used to train OLAM-based artificial neural networks is used to populate the database of training spectra. In an embodiment, the training spectra for an OLAM based artificial neural network comprises one spectrum from each isotope in the 'NORM' class comprising radioactive isotopes such as Ra-226, Tl-208/Th-232, K-40, and U-238; and one spectrum from each isotope belonging to the 'other' class comprising isotopes such as, but not limited to Am-241, Co-57, Ba-133, Cs-137. As is known, isotopes belonging to the 'other' class encompasses more isotopes than are available to obtain, as some of these isotopes decay rapidly and are difficult to collect in an industrial setting, while others are special nuclear materials tightly controlled by government regulations. In various embodiments of the present specification, energy spectra of a large number of isotopes belonging to the 'other' class are collected in order to populate the training set of the OLAM based artificial neural network. In embodiments, a single class of isotopes comprises an energy histogram/scaled energy spectra from each isotope that belongs to that class. In an embodiment of the present specification the OLAM based neural network is trained to classify isotopes into two classes, i.e. 'NORM' and 'other'. In other embodiments, the method of the present specification may be extended to identify a plurality of different pairs of isotope classes, such as, but not limited to 'MEDICAL' and 'OTHER'; or special nuclear materials, i.e. 'SNM' and 'OTHER'.

At step 304, energy spectra generated by an object being inspected in a radiation inspection system is gathered using one or more radiation detectors of the system. At step 306, the gathered energy spectra are normalized by using one or more predefined normalization techniques. At step 308, the normalized spectra are energy scaled by using one or more predefined energy weighting techniques. In an embodiment, predefined weights are applied to the gathered energy spectra to form a weighted matrix of said spectra by using Spectrum Dose Index (SDI) technique. At step 310, the normalized and scaled spectra is fitted to each of the training spectra in the database. In an embodiment, the normalized and scaled spectra is fitted to each of the training spectra in the database in a sequential fashion. In an embodiment, where an OLAM based neural network is used for classification of isotopes, a set of coefficients for each class of the training spectra are applied sequentially to the gathered unknown scaled spectra. In another embodiment, the scaled spectra is fitted across all of the training sets simultaneously.

At step 312, a residual of fitting the normalized scaled spectra with respect to each of the training spectra classes is determined. At step 314 the normalized scaled spectra is identified as belonging to the class of training spectra that results in the smallest residual as determined at step 312. In an embodiment, the training spectra belong to a 'NORM' category, and the normalized scaled spectra that results in a residual ('r') value (as determined in step 312) being less than a predefined threshold value, is determined as belonging to the 'NORM' category; while the normalized scaled spectra that results in a residual value (as determined in step 312) being greater than a predefined threshold value, is determined as belonging to the 'other' category. In an embodiment, the threshold value is determined empirically after the OLAM neural network is trained and all the residual values are determined. In embodiments, the residual values of isotopes belonging to the NORM class must be lower than the residual values of all other isotopes in the normalized scaled spectra. For example, if with respect to a normalized scaled spectra the residual values for NORM sources range from 2.4 to 20.5 and the residual values of all other isotopes range from 27.2 to 115.3, the threshold value may be defined as 23.85 which is half way between 20.5 and 27.2. In other embodiments, the threshold value may be predefined using other suitable techniques.

In a training scenario, radiation spectra are acquired to generate an experimental class that represents a predefined number of radionuclides belonging to the Naturally Occurring Radioactive Materials (NORM) group. Table 1 (below) illustrates all training radionuclides acquired with each corresponding vector symbol.

TABLE 1

| Radionuclide | Vector Symbol |
| --- | --- |
| Ra-226 | Ra |
| K-40 | K |
| Th-232 | Th |

For conducting the training experiment, a background spectrum ($Bkg \in R^{Nc}$) was first collected. Subsequently, a radiation spectrum was acquired for 60 seconds, wherein $Nc=256$ channels from a PVT detector.

Each acquired spectrum vector is represented as a vector $v \in R^{Nc}$ with the i-th individual element being v[i]. The preprocessed spectrum $\tilde{v} \in R^{Ne}$ was calculated considering $\forall i = \{1, 2, \ldots, N_C\}$ by using the equation:

$$\tilde{v}[i] = \begin{cases} \dfrac{i}{v}(v[i] - Bkg[i]) & \text{when } v[i] - Bkg[i] > 0 \\ 0 & \text{when } v[i] - Bkg[i] \le 0 \end{cases} \quad \text{(Equation 2)}$$

where normalization is performed using both $$v \triangleq \sum_{j=1}^{Nc} (v[j] - Bkg[j])$$

and wherein 'i' is the SDI constant.

Figures 3B, 3C:
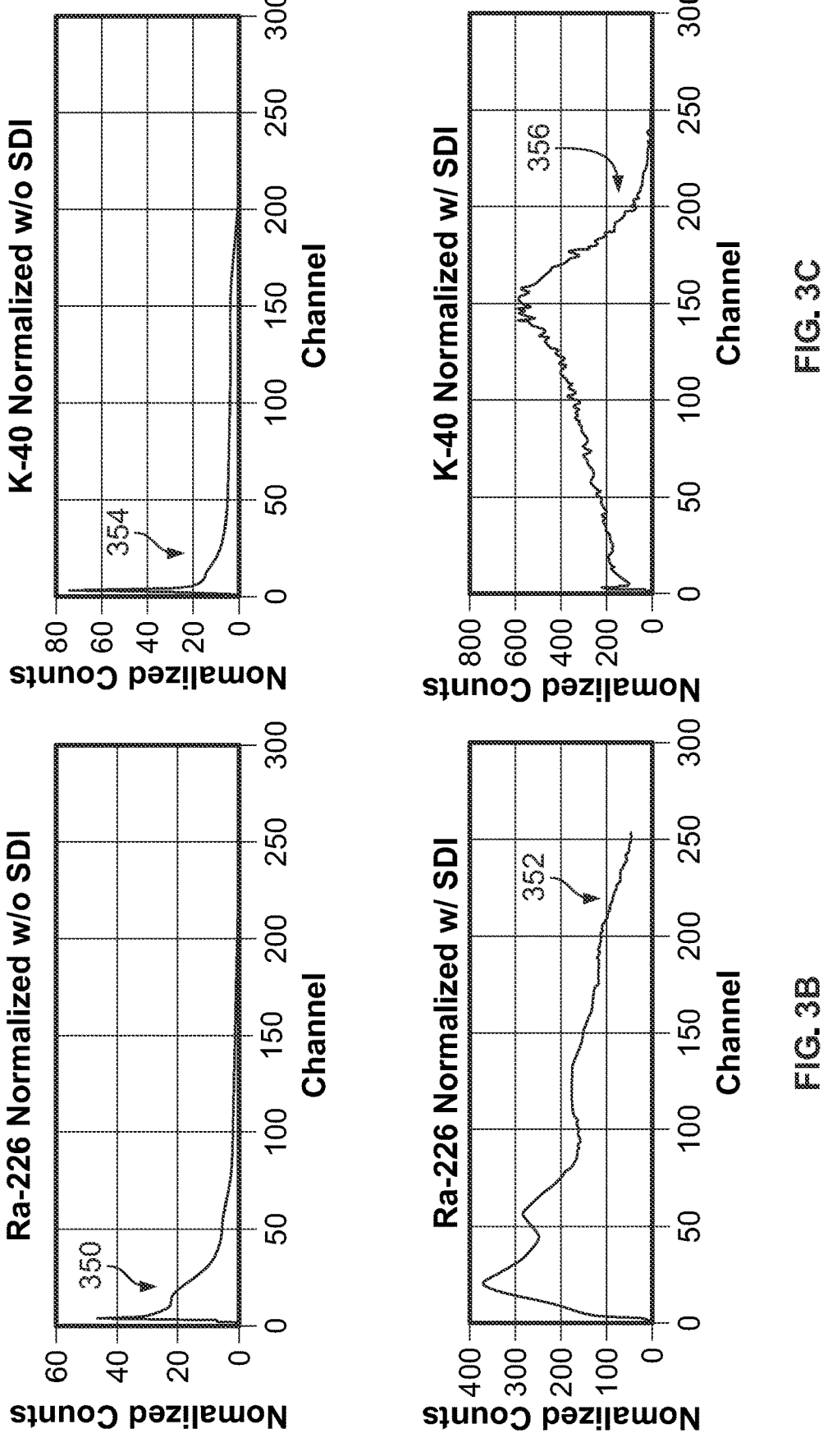
FIG. 3B shows normalized radiation spectra of a radionuclide Ra-226 normalized with and without using the SDI constant in accordance with an embodiment of the present specification.
FIG. 3C illustrates normalized radiation spectra of a radionuclide K-40 normalized with and without using the SDI constant in accordance with an embodiment of the present specification.

FIG. 3B illustrates normalized radiation spectra of a radionuclide Ra-226 normalized with and without using the SDI constant as shown in Equation 2 above. Graph 350 illustrates an Ra-226 spectrum normalized without using the SDI constant, and graph 352 illustrates an Ra-226 spectrum normalized by using the SDI constant. As can be seen, in graph 352 the spectral features, in particular at the higher channels, are more pronounced for enhanced spectral comparison.

FIG. 3C illustrates normalized radiation spectra of a radionuclide K-40 normalized with and without using the SDI constant as shown in Equation 2 above. Graph 354 illustrates an K-40 spectrum normalized without using the SDI constant, and graph 356 illustrates a K-40 spectrum normalized by using the SDI constant. As can be seen, in graph 356 the spectral features, in particular at the higher channels, are more pronounced for enhanced spectral comparison.

Figures 3D, 3E:
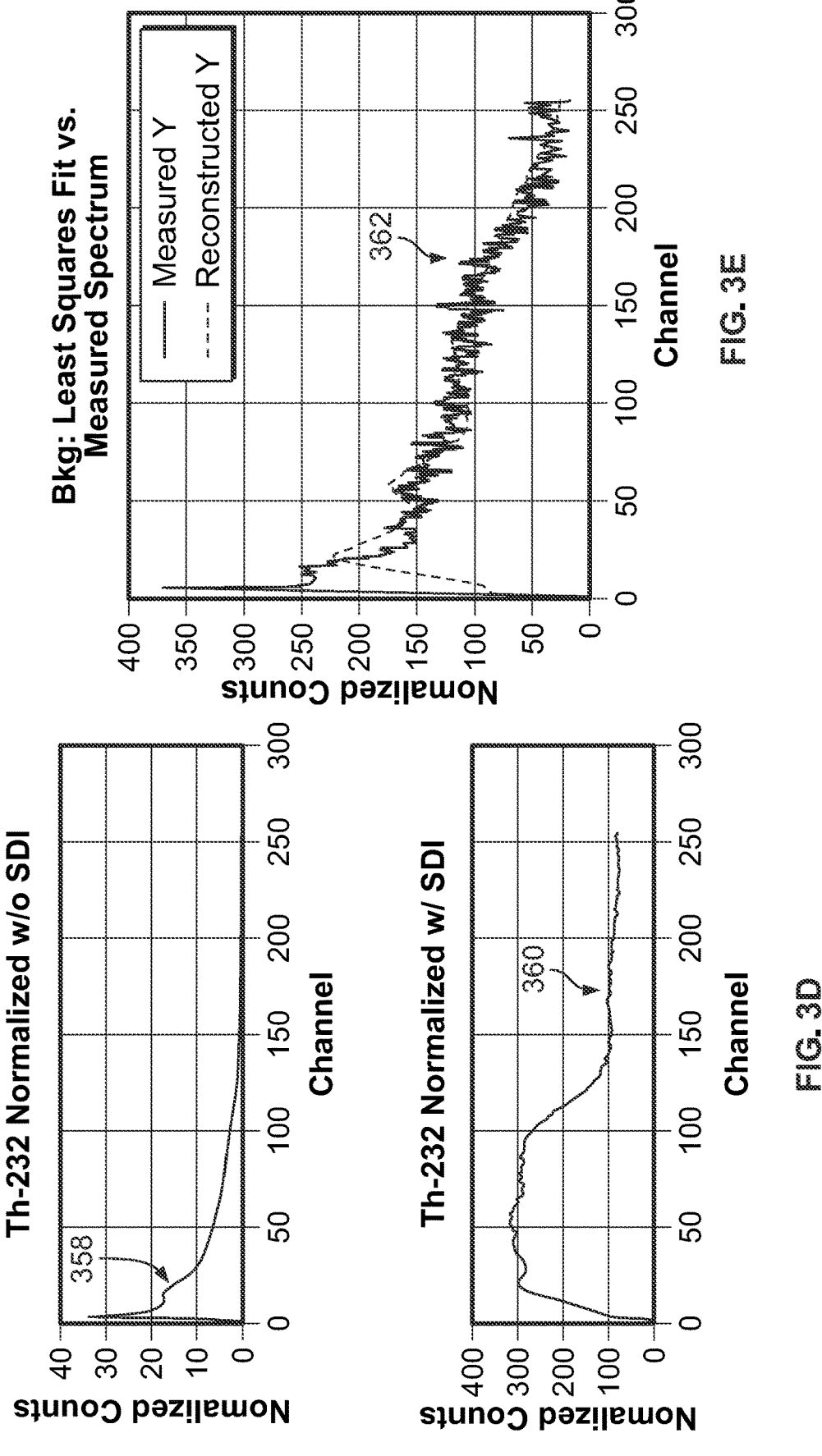
FIG. 3D illustrates normalized radiation spectra of a radionuclide Th-232 normalized with and without using the SDI constant in accordance with an embodiment of the present specification.
FIG. 3E is a graph showing fit discrepancy using background spectrum of a NORM material, in accordance with an embodiment of the present specification.

FIG. 3D illustrates normalized radiation spectra of a radionuclide Th-232 normalized with and without using the SDI constant as shown in Equation 1 above. Graph 358 illustrates a Th-232 spectrum normalized without using the SDI constant, and graph 360 illustrates a Th-232 spectrum normalized by using the SDI constant. As can be seen, in graph 360 the spectral features, in particular at the higher channels, are more pronounced for enhanced spectral comparison.

During training the set of processed training spectrum may be written more compactly as the matrix:

$$A \in R^{Nc \times Nt} \quad \text{(Equation 3)}$$

consisting of the column vectors of spectrum where $N_t=3$ is the number of training vectors.

$$A \triangleq \left\langle \tilde{Ra} \middle| \tilde{K} \middle| \tilde{Th} \right\rangle \quad \text{(Equation 4)}$$

Measured spectra for classification, denoted by:

$$y \in R^{Nc} \quad \text{(Equation 5)}$$

were also acquired for 60 seconds from a PVT detector having $N_c=256$ channels. Again, each measured spectrum was normalized in the same manner and denoted by $\tilde{y}$.

Conceptually, if measured spectrum $\tilde{y}$ is reconstructed using a linear combination of training spectrum, the system may be represented by the matrix equation:

$$\tilde{y} = A\theta \quad \text{(Equation 6)}$$

where $\theta \in \mathbb{R}^{N_t}$ are the weights for each training spectrum.

A solution does not exist for this overdetermined problem since 'A' is not full rank. A matrix is said to have full rank if its rank equals the largest possible for a matrix of the same dimensions, which is the lesser of the number of rows and columns. Hence, the linear least squares solution $\hat{\theta}$ was used to solve for the coefficients using:

$$\hat{\theta} = (A^T A)^{-1} A^T \tilde{y} \quad \text{(Equation 7)}$$

These coefficients may be used to reconstruct the measured spectrum, where the reconstructed vector is denoted by $\hat{y}$ by projecting the measured vector $\tilde{y}$ back into the space spanned by the columns of the training matrix 'A' according to:

$$\hat{y} = A\hat{\theta} \quad \text{(Equation 8)}$$

As is known a residual is a measure of how well a line fits an individual data point. Hence, residuals from a fitted model are defined as the differences between the response data and the fit to the response data at each predictor value:

$$\text{residual} = \text{data} - \text{fit.}$$

The resulting residuals for each channel from reconstruction consist of the vector: $r \in \mathbb{R}^{Nc}$, are an essential component of classification, and are defined by:

$$r \triangleq \tilde{y} - \hat{y} \quad \text{(Equation 9)}$$

The residual vector calculation may be simplified into a single matrix by calculating the projection matrix 'P' that projects the measured spectrum vector $\overline{y}$ into the null space of training matrix 'A' according to:

$$r = \tilde{y} - A(A^T A)^{-1} A^T \tilde{y} \quad \text{(Equation 10)}$$
$$r = [I - A(A^T A)^{-1} A^T] \tilde{y}$$
$$r = P\tilde{y}$$

where 'I' is the identity matrix and $$P \triangleq I - A(A^T A)^{-1} A^T \quad \text{(Equation 11)}$$

In an embodiment, the classification method does not attempt to classify multiple classes simultaneously because reconstruction may result in negative weights that do not make physical sense. Rather, when a measured spectrum is not used in training, the fit often results in a large residual and as a result, misclassification. Hence, in an embodiment, only spectra of a single class are trained at a time for a binary decision indicating whether that class is a member or not. When a measured spectrum of a different class is encountered, the residual is used as a basis of classification.

In order to obtain a size of the residual as compared to the total size of the measured spectrum, in an embodiment, the size of the residual vector is divided by the size of the measured spectrum by using a simple decimal fraction. This indicates proportionally how large the fitted vector's residual is compared to the original spectrum. The magnitude or size of each vector is calculated as the sum of the absolute values of each element or in compact notation the $L^1$ Norm function denoted by $\|v\|_1$ for a measured vector v. Consequently, the relative residual scalar $\hat{r}$ used for classification may be obtained by:

$$\hat{r} = 100\left(\frac{\|P\hat{y}\|_1}{\|\hat{y}\|_1}\right)$$ (Equation 12)

Since, the relative residual is large when using a measured vector $\overline{y}$ that is not a member of the trained class and small when it is a member of the class, in an embodiment, the present specification provides a simple threshold created empirically using experimental data, as described above with respect to step 312 of FIG. 3.

FIG. 3E is a graph illustrating a fit discrepancy using background spectrum of a NORM material, in accordance with an embodiment of the present specification. Fit discrepancy defines how well a measured spectrum, which in this case, comprises NORM isotopes in a majority concentration as these naturally occurring isotopes produce a gamma radiation background, fits a training spectrum of a NORM material. Graph 362 illustrates the accuracy of the fit resulting in a small relative residual: $\hat{r}$=16.9.

Table 2 shows values for the measured spectra of a plurality of 'other' (non-NORM) materials along with their corresponding relative residual values. It can be seen in Table 2 that all of the illustrated relative residual values are significantly higher than the relative residual value for background, i.e. $\hat{r}$=16.9.

TABLE 2

| Radionuclide | Vector Symbol | $\hat{r}$ |
|---|---|---|
| Am-241 | Am-241 | 170.8 |
| Co-57 | Co-57 | 163.2 |
| Ba-133 | Ba-133 | 109.2 |
| Cs-137 | Cs-137 | 76.5 |
| Co-60 | Co-60 | 25.3 |

Figures 3F, 3G:
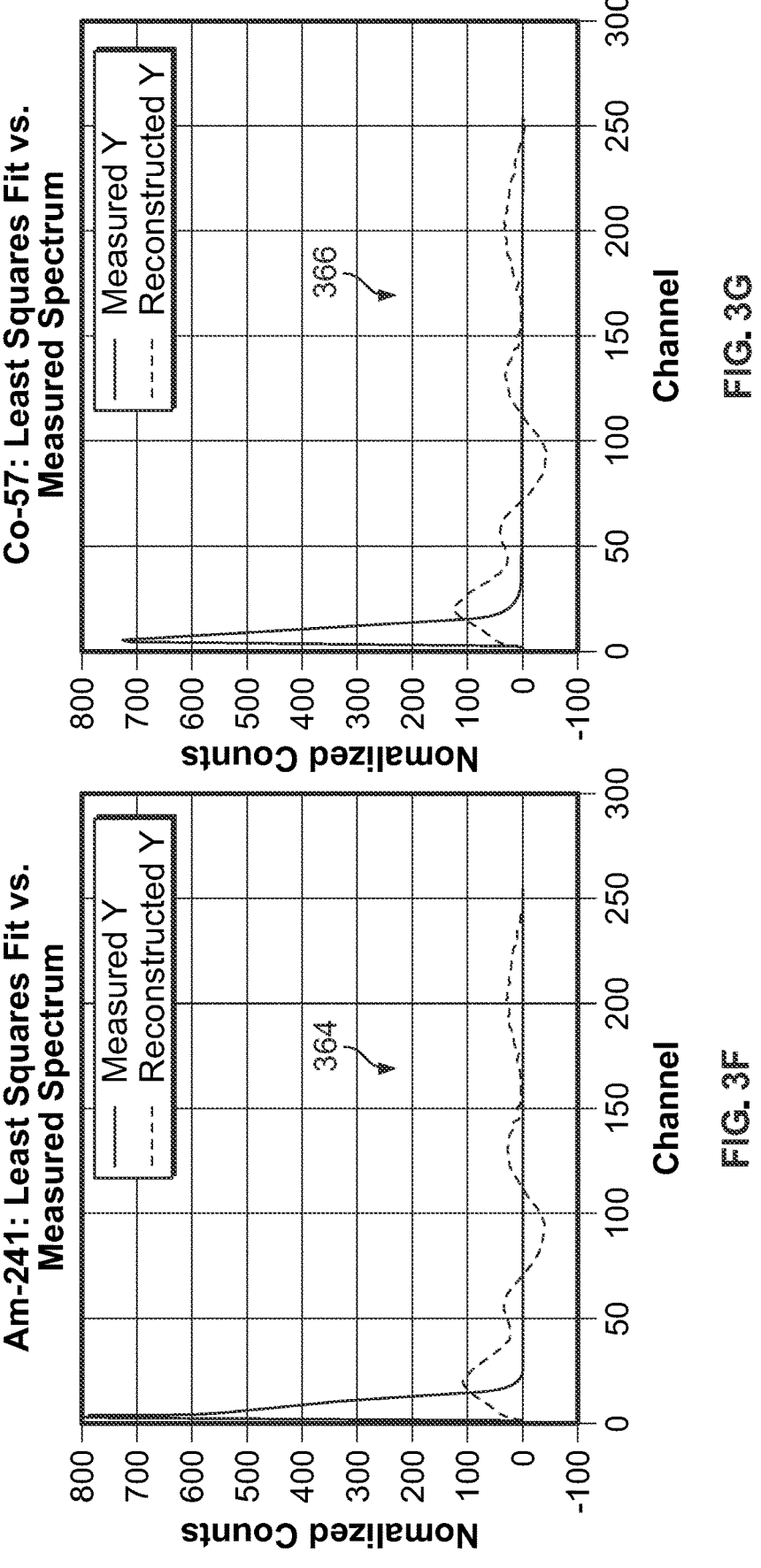
FIG. 3F a graph showing a fit discrepancy using the radionuclide Am-241, in accordance with an embodiment of the present specification
FIG. 3G is a graph showing fit discrepancy using the radionuclide Co-57, in accordance with an embodiment of the present specification.
Figures 3H, 3I:
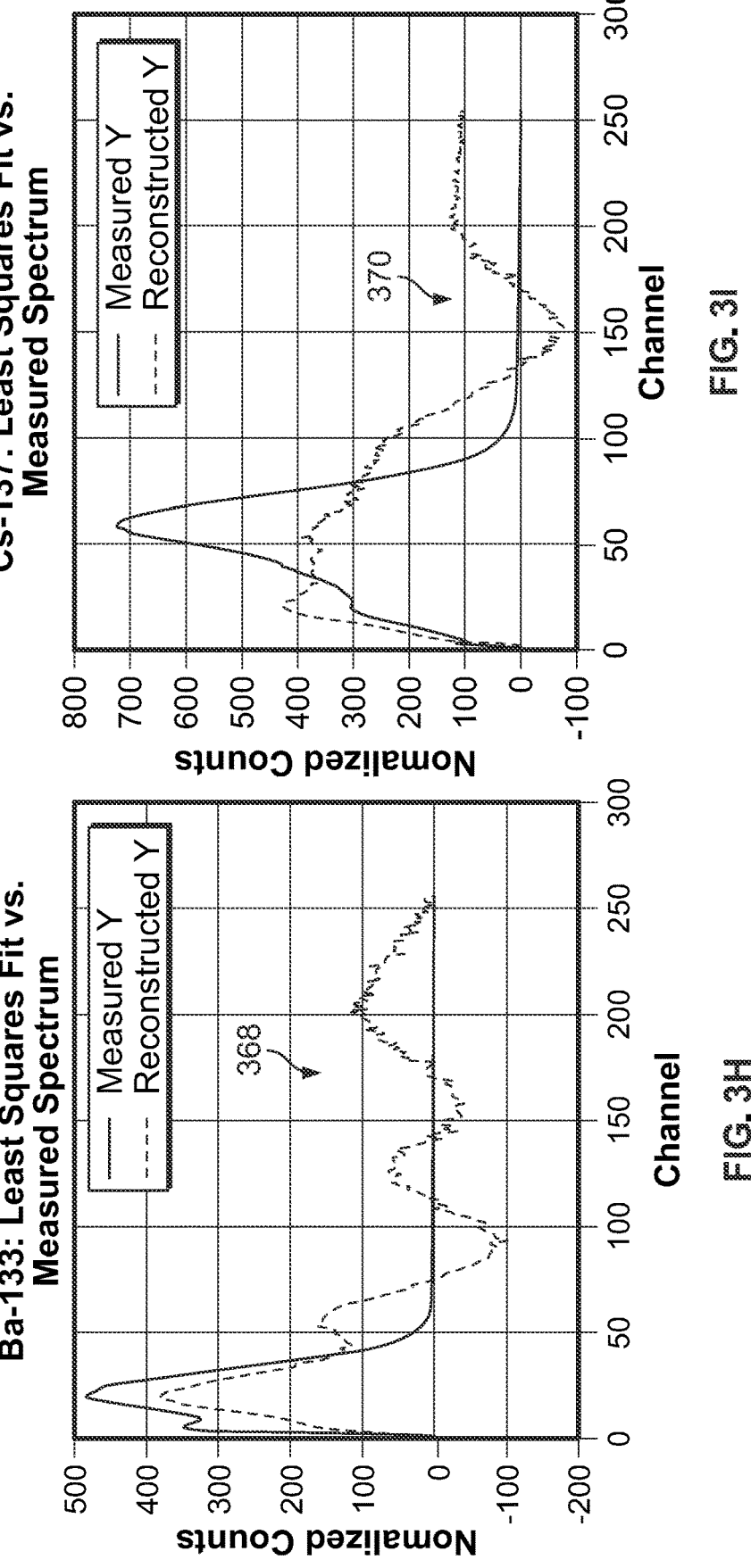
FIG. 3H is a graph showing fit discrepancy using the radionuclide Ba-133, in accordance with an embodiment of the present specification.
FIG. 3I is a graph showing fit discrepancy using the radionuclide Cs-137, in accordance with an embodiment of the present specification.
Figure 3J:
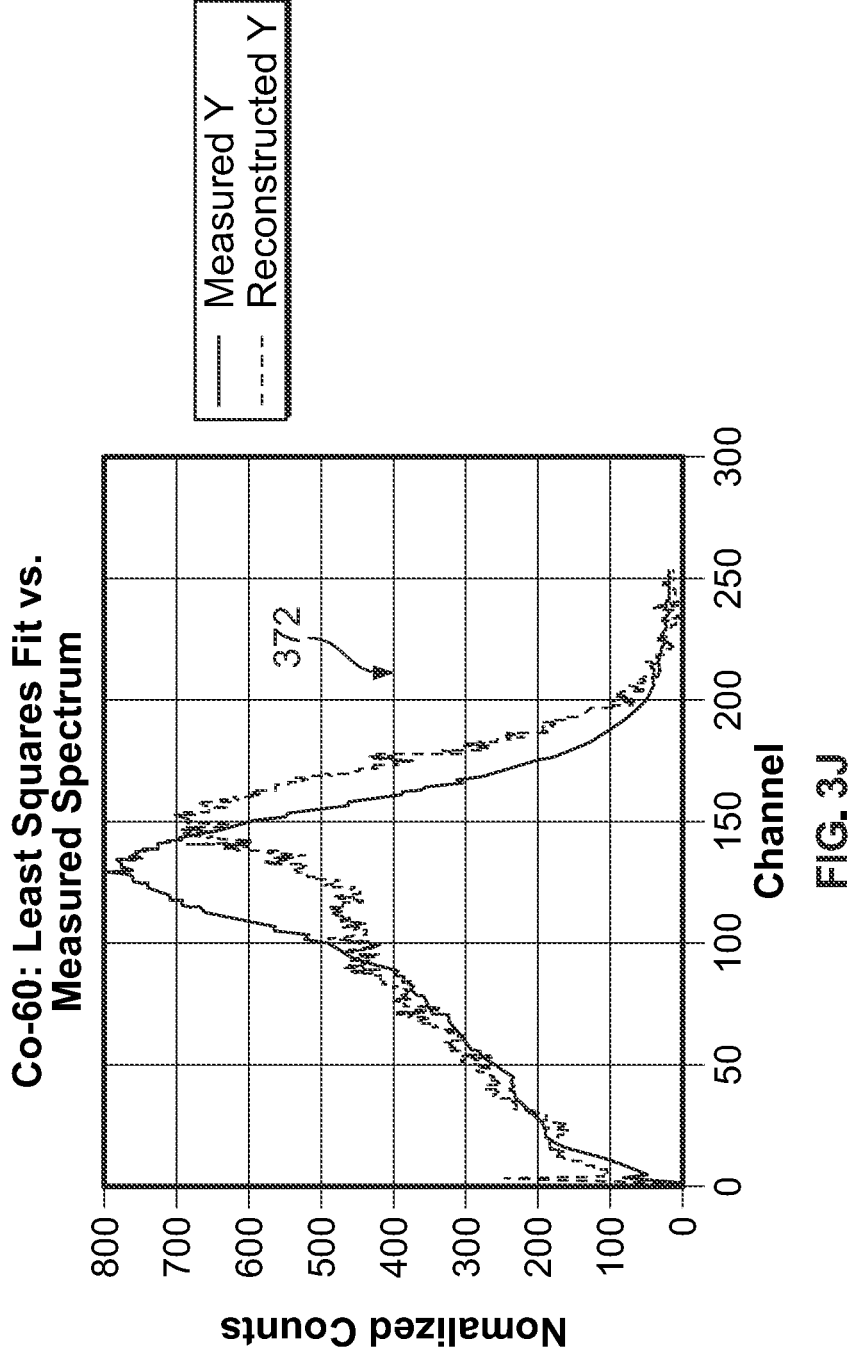
FIG. 3J is a graph showing fit discrepancy using the radionuclide Co-60, in accordance with an embodiment of the present specification.

FIG. 3F is a graph 364 showing a fit discrepancy using the radionuclide Am-241, in accordance with an embodiment of the present specification. FIG. 3G is a graph 366 showing a fit discrepancy using the radionuclide Co-57, in accordance with an embodiment of the present specification. FIG. 3H is a graph 368 showing a fit discrepancy using the radionuclide Ba-133, in accordance with an embodiment of the present specification. FIG. 3I is a graph 370 showing a fit discrepancy using the radionuclide Cs-137, in accordance with an embodiment of the present specification. FIG. 3J is a graph 372 showing a fit discrepancy using the radionuclide Co-60, in accordance with an embodiment of the present specification.

Figures 4A, 4B:
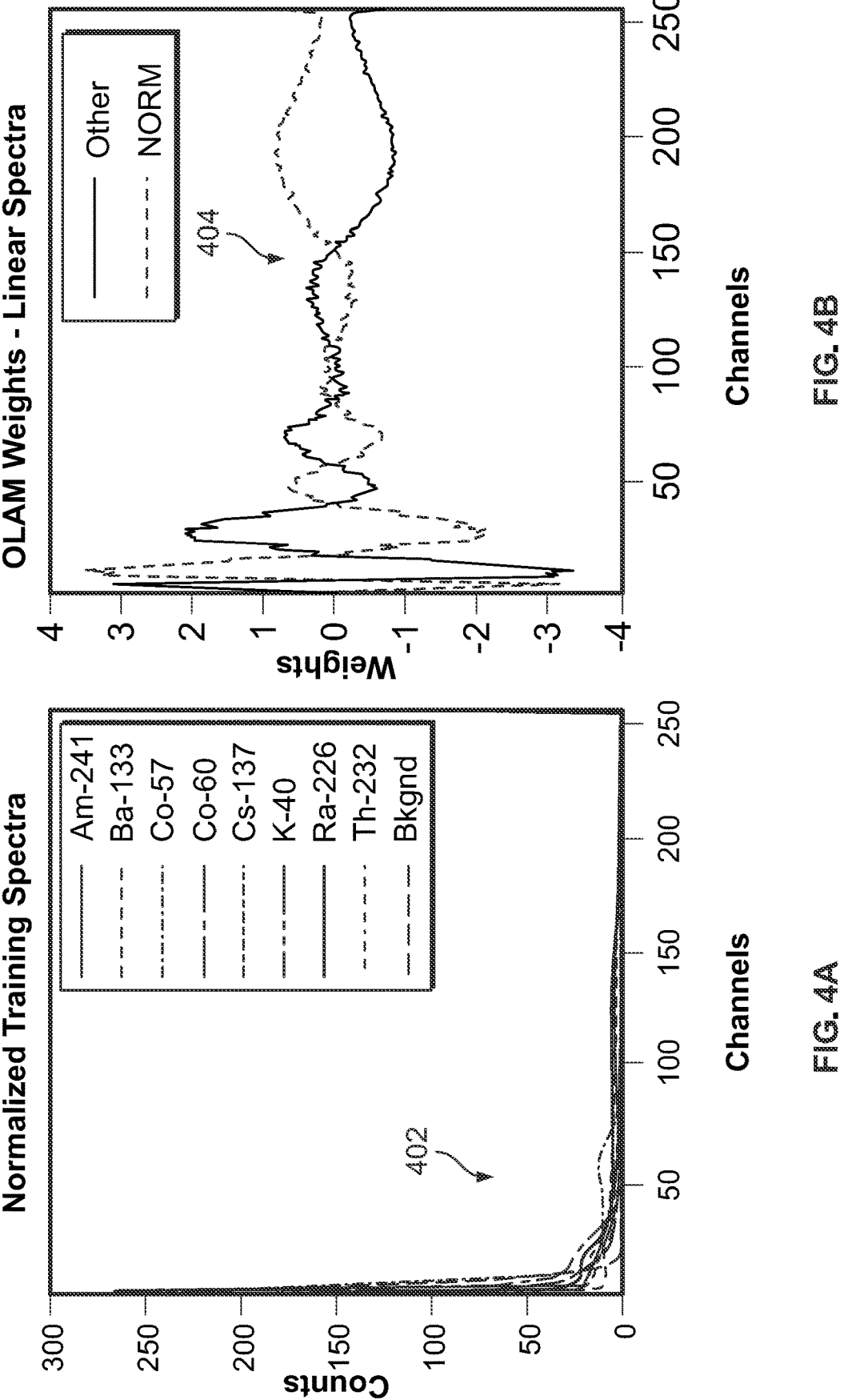
FIG. 4A illustrates normalized radiation spectra for a plurality of isotopes, in accordance with an embodiment of the present specification.
FIG. 4B illustrates the spectra shown in FIG. 4A weighted and categorized into 'NORM' or 'other' categories.

FIG. 4A is a graph 402 illustrating normalized radiation spectra for a plurality of isotopes, in accordance with an embodiment of the present specification. FIG. 4B is a graph 404 illustrating the spectra shown in FIG. 4A weighted and categorized into 'NORM' or 'other' categories. Since, the NORM isotopes typically emit higher energy gamma radiation, in embodiments, the energy scaling of the radiation spectra by using a weighting matrix enables a classification algorithm (such as OLAM) to categorize the spectra in real time into NORM or 'other' categories by identifying the high energy NORM isotopes.

In an exemplary test case a plurality of detected radiation spectra along with background spectra was analyzed by using the categorization method of the present specification. The background spectra comprise NORM isotopes in a majority concentration as these naturally occurring isotopes produce a gamma radiation background. By using a classification algorithm such as OLAM, approximately 80% of the background was categorized to the NORM category, while 20% to the 'other' category. On applying the same energy scaling and classifying algorithms to a Cs-137 spectrum collected from each of four PVT detectors deployed in a radiation inspection system, and to the sum of the four PVT detectors, approximately 80% of the spectra was categorized to the 'other' category and 20% to the NORM category, since the Cs-137 spectra collected included background radiation as well. In various embodiments, the method of the present specification may be used to identify a plurality of different pairs of isotope classes, such as, but not limited to 'MEDICAL' and 'OTHER'; or special nuclear materials, i.e. 'SNM' and 'OTHER'.

The above examples are merely illustrative of the many applications of the systems, apparatuses, and methods of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A radiation portal monitor comprising:
a processing system; and,
a plurality of detectors in data communication with the processing system wherein the processing system is configured to determine if radiation spectra comprises radiation corresponding to naturally occurring radiation material (NORM) sources by:
generating a database of training spectra, each of the training spectra in the database representing a NORM material;
obtaining the radiation spectra;
normalizing the obtained radiation spectra by using one or more predefined normalization techniques;
energy scaling the normalized radiation spectra by using one or more energy scaling techniques;
fitting the normalized, scaled radiation spectra to at least a portion of the training spectra in the database;
determining a residual generated from fitting the normalized, scaled radiation spectra with respect to said portion of the training spectra; and identifying the normalized, scaled radiation spectra as representing a NORM material based on the residual and a threshold value.

2. The radiation portal monitor of claim 1 wherein the normalized, scaled radiation spectra is determined as representing a NORM material when the residual is less than the threshold value.

3. The radiation portal monitor of claim 1 wherein the processor is further configured to identify the normalized, scaled radiation spectra as belonging to an 'other' category when the residual is greater than the threshold value.

4. The radiation portal monitor of claim 1 wherein the processor is configured to determine the threshold value empirically based on the training spectra and the residual of fitting the normalized scaled radiation spectra with a class of the training spectra.

5. The radiation portal monitor of claim 1 wherein obtaining the radiation spectra comprises gathering energy spectra radiated by an object being inspected in the radiation portal monitor by using one or more of the plurality of detectors.

6. The radiation portal monitor of claim 1 wherein energy scaling the normalized radiation spectra comprises applying predefined weights to the obtained radiation spectra to obtain a weighted matrix of said obtained radiation spectra.

7. The radiation portal monitor of claim 1 further comprising Optimal Linear Associative Memory (OLAM) based artificial neural networks trained by one or more of said training spectra.

8. The radiation portal monitor of claim 1 further comprising an Optimal Linear Associative Memory (OLAM) neural network implemented within a field-programmable gate array (FPGA) integrated circuit, wherein the OLAM neural network implemented within the FPGA is configured to determine when the radiation spectra comprises radiation corresponding to NORM materials.

9. The radiation portal monitor of claim 1 wherein the normalized, scaled radiation spectra is fitted to each of the training spectra in the database in a sequential fashion.

10. The radiation portal monitor of claim 1 wherein the NORM material is at least one of: Ra-226, Th-232/Tl-208, K-40, and U-238.

11. The radiation portal monitor of claim 5 wherein the plurality of detectors are large-area low-resolution radiation detectors.

12. The radiation portal monitor of claim 5 wherein the plurality of detectors are polyvinyltoluene (PVT) detectors.

13. The radiation portal monitor of claim 5 wherein the plurality of detectors are gamma radiation detectors.

14. The radiation portal monitor of claim 5 wherein the radiation portal does not include a radiation source.

15. The radiation portal monitor of claim 5 wherein the radiation portal is a passive radiation portal monitor (RPM) used to detect presence of ionizing radiation sources passing through the RPM.

16. The radiation portal monitor of claim 15 wherein the RPM comprises a plurality of panels, wherein opposing ones of the plurality of panels are spaced to enable a cargo container to pass between said opposing ones of the plurality of panels.

17. The radiation portal monitor of claim 16 wherein each of the plurality of panels comprises a radiation detector.

18. The radiation portal monitor of claim 6 wherein the one or more energy scaling techniques add more weight to higher energies in the normalized radiation spectra for aiding in determination of NORM materials.

19. The radiation portal monitor of claim 7 wherein the training spectra for the OLAM based artificial neural networks comprise one spectrum from each isotope of the NORM material.

* * * * *